United States Patent
Atkins, Jr. et al.

(10) Patent No.: US 11,935,658 B1
(45) Date of Patent: Mar. 19, 2024

(54) METHOD AND SYSTEM FOR RELEVANCE-BASED MEDICATION SEARCH

(71) Applicant: ENT Solutions Group LLC, San Antonio, TX (US)

(72) Inventors: James H. Atkins, Jr., San Antonio, TX (US); Lori Jean Atkins, San Antonio, TX (US)

(*) Notice: Subject to any disclaimer, the term of this patent is extended or adjusted under 35 U.S.C. 154(b) by 210 days.

(21) Appl. No.: 16/917,884

(22) Filed: Jun. 30, 2020

Related U.S. Application Data

(60) Provisional application No. 62/869,561, filed on Jul. 1, 2019.

(51) Int. Cl.
*G16H 50/70* (2018.01)
*G06F 16/9535* (2019.01)
*G16H 10/60* (2018.01)
*G16H 20/10* (2018.01)
*G16H 70/40* (2018.01)

(52) U.S. Cl.
CPC ......... *G16H 50/70* (2018.01); *G06F 16/9535* (2019.01); *G16H 10/60* (2018.01); *G16H 20/10* (2018.01); *G16H 70/40* (2018.01)

(58) Field of Classification Search
CPC ......... G16H 20/10; G16H 70/40; G16H 40/20
See application file for complete search history.

(56) References Cited

U.S. PATENT DOCUMENTS

2019/0304604 A1\* 10/2019 Kupersmith ........... G16H 50/70

FOREIGN PATENT DOCUMENTS

WO  WO-2016154387 A1 \* 9/2016 ....... G06F 17/30551

OTHER PUBLICATIONS

Kuhn, Michael, et al. "The SIDER database of drugs and side effects." Nucleic acids research 44. D1 (2016): D1075-D1079. (Year: 2016).\*

\* cited by examiner

*Primary Examiner* — Jason B Dunham
*Assistant Examiner* — Constantine Siozopoulos
(74) *Attorney, Agent, or Firm* — Campbell Stephenson LLP

(57) ABSTRACT

A method, computer program product, and system are disclosed. The method, when implemented in a computer system, includes obtaining patient information (where the patient information comprises symptom information), and identifying a medication. The medication is identified by searching a medication information database using the symptom information.

20 Claims, 19 Drawing Sheets

US 11,935,658 B1

METHOD AND SYSTEM FOR RELEVANCE-BASED MEDICATION SEARCH

PRIORITY APPLICATION

This application claims the domestic benefit under Title 35 of the United States Code § 119(e) of U.S. Provisional Patent Application Ser. No. 62/869,561, entitled "Method and System For Relevance-Based Medication Search," filed Jul. 1, 2019, which is hereby incorporated by reference in its entirety and for all purposes as if completely and fully set forth herein.

FIELD OF THE INVENTION

The present invention relates to pharmacology, and, more particularly, to methods and systems for relevance-based medication search.

BACKGROUND

Medications, both over-the-counter (OTC) and prescription, are an integral part of daily life for millions of people around the world. However, faced with a vast array of existing and new medications, quickly and efficiently determining the proper medication for a given condition can be difficult, if not impossible, for both medical practitioners (in the case of prescription and OTC medications) and, particularly, laypersons. Complicating matters is the fact that a patient may have other conditions, as well as interactions that may occur between medications. Further considerations include physical characteristics, dosing, the use of generics, and other such issues.

The foregoing problems, as well as other such failings, stand as obstacles to the efficient, effective identification and prescribing of medications. That being the case, it is therefore desirable to provide mechanisms that address such shortcomings, and to do so in an effective, efficient manner.

BRIEF DESCRIPTION OF THE DRAWINGS

The present invention may be better understood, and its numerous objects, features and advantages made apparent to those skilled in the art by referencing the accompanying drawings.

DETAILED DESCRIPTION

The following is intended to provide a detailed description of an example of the invention and should not be taken to be limiting of the invention itself. Rather, any number of variations may fall within the scope of the invention which is defined in the claims following the detailed description.

Introduction

Methods and systems such as those described herein provide the ability to identify one or more appropriate medications, in view of a patient's particular situation (e.g., physical characteristics, known conditions, and the like) and one or more symptoms exhibited/reported by the patient.

Thus, among other advantages, methods and systems such as those described herein, methods and systems such as those described herein provide the ability of a user to identify one or more medications that can be prescribed (or procured) to address the patient's illness and/or symptoms.

Example Network Architecture

Figure 1:
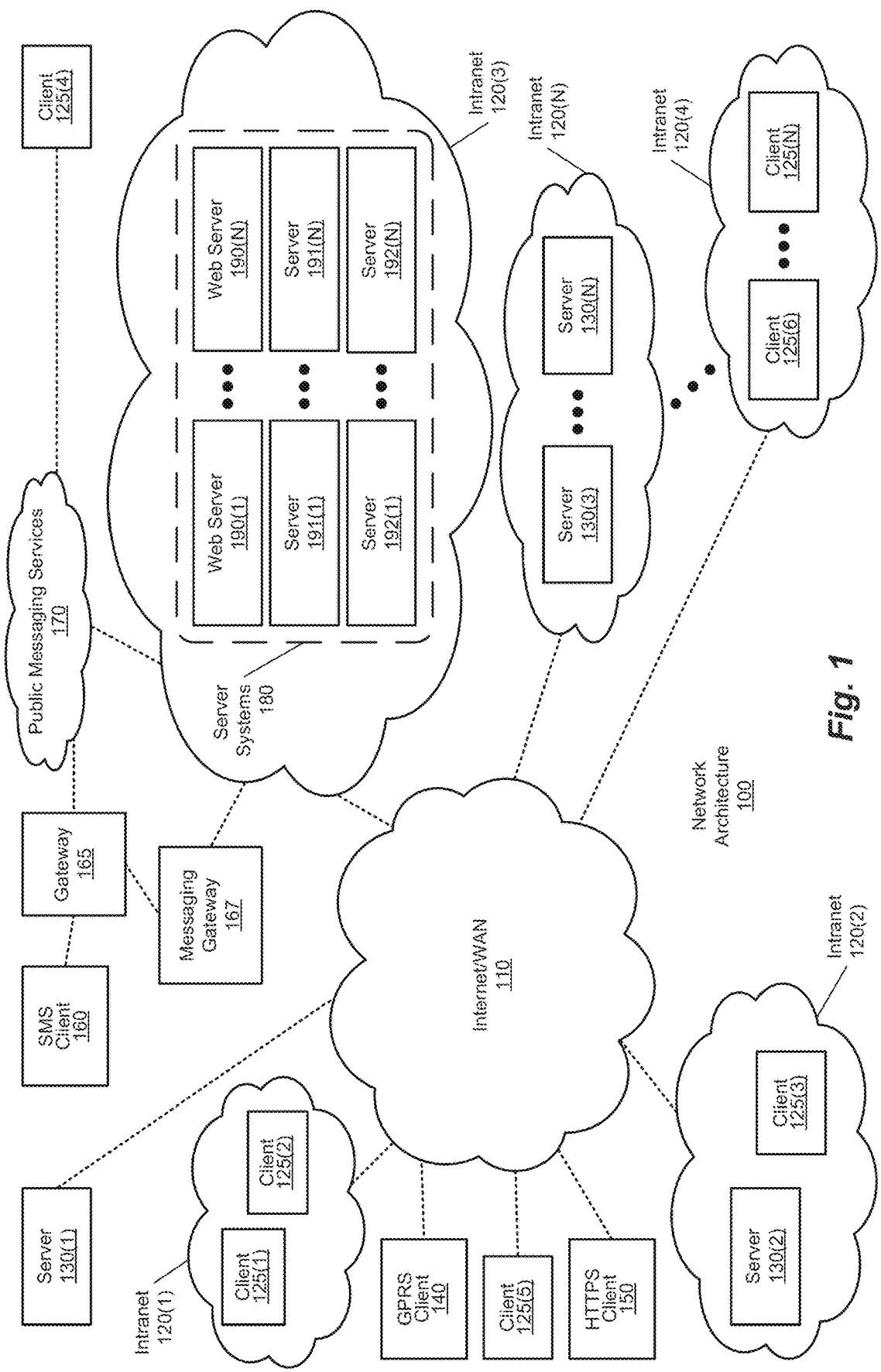
FIG. 1 is a block diagram illustrating an example of a network architecture, according to methods and systems such as those disclosed herein.

FIG. 1 is a block diagram illustrating an example of a network architecture 100 that includes server systems and other components, according to one embodiment. Network architecture 100 includes an internetwork (depicted in FIG. 1 as an internet/wide area network (WAN) 110), which is configured to couple a number of intranets to one another (depicted in FIG. 1 as intranets 120(1)-(N)). Intranets 120(1)-(N), in turn, can include a number of components, such as one or more clients (depicted in FIG. 1 as clients 125(1)-(N)) and/or servers (depicted in FIG. 1 as servers 130(1)-(N)). Clients 125(1)-(N) and/or servers 130(1)-(N) can, for example, be implemented using computer systems such as those described subsequently. Internet/WAN 110 thus communicatively couples intranets 120(1)-(N) to one another, thereby allowing clients 125(1)-(N) and servers 130(1)-(N) to communicate with one another (and can, in certain embodiments, provide for the servers of intranets 120(3) and 120(N), for example, to operate as cloud-based server systems). As is depicted in FIG. 1, clients 125(1)-(N) can be communicatively coupled to one another and to servers 130(1)-(N) as part of one of intranets 120(1)-(N), or directly via internet/WAN 110. Similarly, servers 130(1)-(N) can be coupled via intranet/WAN 110 via a direct connection to intranet/WAN 110, or as part of one of intranets 120(1)-(N).

Network architecture 100 also provides for communication via intranet/WAN 110 using one or more other devices. Such devices can include, for example, a general packet radio service (GPRS) client 140 (e.g., a "smart phone," a "tablet" computer, or other such mobile device), a secure web client (depicted in FIG. 1 as a secure hypertext transfer protocol client 150), and a basic cellular phone (e.g., using standard texting or other communication protocols, and depicted in FIG. 1 as a simple messaging service (SMS) client 160). HTTPS client 150 can be, for example, a laptop computer using the HTTP Secure (HTTPS) protocol. Support for GPRS clients, SMS clients, HTTP clients, and the like thereby provide users with communication functionality according to an embodiment in a mobile environment. As is also depicted in FIG. 1, SMS client 160 can communicate via internet/WAN 110 via several channels. SMS client 160 can communicate directly, for example, with a gateway 165, which, in turn, communicates with internet/WAN 110 via a messaging gateway 167 and, optionally, elements within intranet 120(3), for example. Alternatively, SMS client 160 can, via gateway 165, communicate with intranet 120(3) (and so, internet/WAN 110) via public messaging services 170 to which gateway 165 and intranet 120(3) are connected. As is also depicted in FIG. 1, a client 125(4) is also able to communicate via internet/WAN 110 by way of public communication services 170 and intranet 120(3). In order to support such communications, as well as other communications according to various embodiments, intranet 120(3) includes server systems 180, as well as (optionally) providing for a number of clients (not shown), in the manner of intranet 120(2).

Server systems 180 include a number of components that allow server systems 180 to provide various functionalities (e.g., supporting various communications, web-based services, cloud-based services, enterprise services, and so on). Among these components, in certain embodiments, are a number of servers, which can be implemented in hardware and/or software. Examples of such servers include web servers (depicted in FIG. 1 as web servers 190(1)-(N), servers 191(1)-(N)), and servers 192(1)-(N). As will be appreciated in light of the present disclosure, servers 191(1)-(N) and servers 192(1)-(N) are merely (and only generically) representative of servers and their configurations that can be employed in the implementation of methods and systems such as those disclosed herein. Further in this regard, while server systems 180 are depicted, at least to some extent, as being centrally located (or at least, co-located), such is the case simply for ease of presentation. As will be appreciated in light of the present disclosure, server systems 180 can themselves be implemented in a distributed manner.

Servers such as those included in server systems 180 comprehend hardware and/or software configured to facilitate functionalities that support operations according to the concepts disclosed herein, among other possible such components and mechanisms, in communication with one another (e.g., directly, via various application programming interfaces (APIs) and/or other such interfaces, and/or other such mechanisms and/or constructs). As will be discussed in greater detail in connection with subsequent figures, the server systems of server systems 180 provide such functionality, for example by presenting end-users with a website (functionality effected by, for example, web servers 190(1)-(N)) or functionality presented to users by way of a software program such as a mobile application ("app"). In so doing, web servers 190(1)-(N) present information collected, generated, organized, and maintained by one or more servers 191(1)-(N) and/or servers 192(1)-(N). Such a website can be accessed by an end-user using a client computing device such as one or more of clients 125(1)-(N), GPRS client 140, HTTPS client 150, and/or SMS client 160. As will be appreciated in light of the present disclosure, the ability to support such functionality on mobile devices such as those described herein is of importance, as mobile electronic commerce is fast becoming an important facet of today's online environment. In providing functionality such as that described herein, network architecture 100 is able to support the identification and presentation of relevant medication information in an efficient, effective manner.

It will be appreciated that, in light of the present disclosure, the variable identifier "N" is used in several instances in various of the figures herein to more simply designate the final element of a series of related or similar elements (e.g., intranets 120(1)-(N), clients 125(1)-(N), and servers 130(1)-(N)). The repeated use of such variable identifiers is not meant to imply a correlation between the sizes of such series of elements. The use of variable identifiers of this sort in no way is intended to (and does not) require that each series of elements have the same number of elements as another series delimited by the same variable identifier. Rather, in each instance of use, variables thus identified may represent the same or a different value than other instances of the same variable identifier.

As will be appreciated in light of the present disclosure, processes according to concepts embodied by systems such as those described herein include one or more operations, which may be performed in any appropriate order. It is appreciated that operations discussed herein may consist of directly entered commands by a computer system user or by steps executed by application specific hardware modules, but the preferred embodiment includes steps executed by software modules. The functionality of steps referred to herein may correspond to the functionality of modules or portions of modules.

The operations referred to herein may be modules or portions of modules (e.g., software, firmware or hardware modules). For example, although the described embodiment includes software modules and/or includes manually entered user commands, the various example modules may be application specific hardware modules. The software modules discussed herein may include script, batch or other executable files, or combinations and/or portions of such files. The software modules may include a computer program or subroutines thereof encoded on computer-readable storage media.

Additionally, those skilled in the art will recognize that the boundaries between modules are merely illustrative and alternative embodiments may merge modules or impose an alternative decomposition of functionality of modules. For example, the modules discussed herein may be decomposed into submodules to be executed as multiple computer processes, and, optionally, on multiple computers. Moreover, alternative embodiments may combine multiple instances of a particular module or submodule. Furthermore, those skilled in the art will recognize that the operations described in example embodiment are for illustration only. Operations may be combined or the functionality of the operations may be distributed in additional operations in accordance with the invention.

Alternatively, such actions may be embodied in the structure of circuitry that implements such functionality, such as the micro-code of a complex instruction set computer (CISC), firmware programmed into programmable or erasable/programmable devices, the configuration of a field-programmable gate array (FPGA), the design of a gate array or full-custom application-specific integrated circuit (ASIC), or the like.

Each of the blocks of the flow diagram may be executed by a module (e.g., a software module) or a portion of a module, or a computer system user using, for example, a computer system such as computer system 1810, described subsequently in connection with FIG. 18. Thus, the above described method, the operations thereof and modules therefor may be executed on a computer system configured to execute the operations of the method and/or may be executed from computer-readable storage media. The method may be embodied in a machine-readable and/or computer-readable storage medium for configuring a computer system to execute the method. Thus, the software modules may be stored within and/or transmitted to a computer system memory to configure the computer system to perform the functions of the module, for example.

Such a computer system normally processes information according to a program (a list of internally stored instructions such as a particular application program and/or an operating system) and produces resultant output information via I/O devices. A computer process typically includes an executing (running) program or portion of a program, current program values and state information, and the resources used by the operating system to manage the execution of the process. A parent process may spawn other child processes to help perform the overall functionality of the parent process. Because the parent process specifically spawns the child processes to perform a portion of the overall functionality of the parent process, the functions performed by child processes (and grandchild processes, etc.) may sometimes be described as being performed by the parent process.

Such a computer system typically includes multiple computer processes executing "concurrently." Often, a computer system includes a single processing unit that is capable of supporting many active processes alternately. Although multiple processes may appear to be executing concurrently, at any given point in time only one process is actually executed by the single processing unit. By rapidly switching which process is being executed, a computer system gives the appearance of concurrent process execution. The ability of a computer system to multiplex the computer system's resources among multiple processes in various stages of execution is called multitasking. Systems with multiple processing units, which by definition can support true concurrent processing, are called multiprocessing systems. Active processes are often referred to as executing concurrently when such processes are executed in a multitasking and/or a multiprocessing environment.

The software modules described herein may be received by such a computer system, for example, from computer readable storage media. The computer readable storage media may be permanently, removably, or remotely coupled to the computer system. The computer readable storage media may non-exclusively include, for example, any number of the following: magnetic storage media including disk and tape storage media, optical storage media such as compact disk media (e.g., CD-ROM, CD-R, etc.) and digital video disk storage media, nonvolatile memory storage memory including semiconductor-based memory units such as FLASH memory, EEPROM, EPROM, ROM or application specific integrated circuits; volatile storage media including registers, buffers or caches, main memory, RAM, and the like; and other such computer-readable storage media. In a UNIX-based embodiment, the software modules may be embodied in a file, which may be a device, a terminal, a local or remote file, or other such devices. Other new and various types of computer-readable storage media may be used to store the software modules discussed herein.

Example Architectures for a Distributed Manufacturing System

Figure 2:
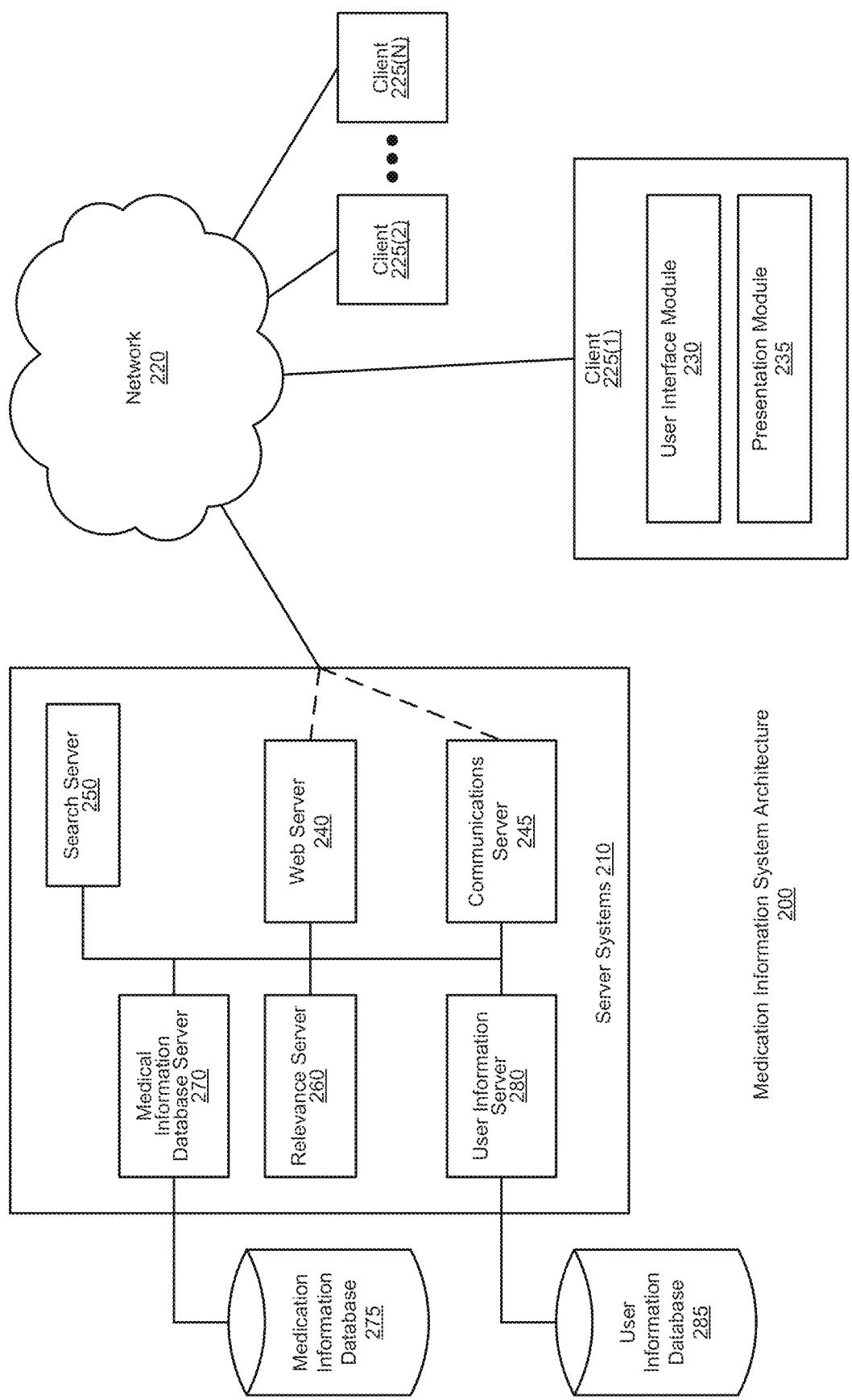
FIG. 2 is a block diagram illustrating an example of a medical information system architecture, according to methods and systems such as those disclosed herein.

FIG. 2 is a block diagram illustrating an example of a medication information system architecture, according to methods and systems such as those disclosed herein. To this end, FIG. 2 depicts a medication information system architecture 200.

Medication information system architecture 200 includes one or more servers (e.g., depicted in FIG. 2 as server systems 210), which can be accessed via a network 220 by one or more clients (e.g., depicted in FIG. 2 as clients 225(1)-(N), or in the aggregate as clients 225). Clients 225 are representative of clients 125 of FIG. 1, and more specifically, can be taken as representing not only desktop, laptop, and comparable computer systems, but also as devices such as GPRS client 40, HTTPS client 150, SMS client 160, and/or the like. Further, as will be appreciated in light of the present disclosure, while medication information system architecture 200 is shown and described as a distributed architecture (e.g., using either a web-based approach or proprietary communications), the components of medication information system architecture 200 can also be implemented as a mobile application (or "app"). Each of clients 225 can support the receipt and/or display of information displayed in a user interface thereof, with such functionality being supported by, for example, a user interface module 230 and a presentation module 235, as may be implemented on one or more of clients 225.

In certain embodiments, server systems 210 can include a Web server 240, a communication server 245, a search server 250, and a relevance server 260. In support of the functionalities provided thereby, a medical information database server 270 accesses a medication information database 275 (e.g., as by reading medication information from and writing medication information to medication information database 275). Medication information database 275 can include information regarding medications (both medications to be suggested as part of the operations of medication information system architecture 200, as well as medication information regarding medication interaction, appropriate applications, contraindications, and the like), symptomologic information, dosing, and other such information. Similarly, a user information server 280 can be provided in order to access a user information database 285. User information database 285 can include information regarding users of the system, patient information (e.g., physical characteristics, medications currently being taken by the patient, information regarding allergic reactions of the patient, and other such information).

In light of the foregoing, the communication paths between various servers are depicted in FIG. 2 as supporting communications between various ones of the servers of medication information system architecture 200. Web server 240, in turn, is depicted as being in communication with the servers depicted therein. Communications server 245 also provides for communications with various of the servers. In the embodiment depicted in FIG. 2, web server 240 provides for the presentation of one or more webpages in support of receiving information from users and presenting information to users. Communications server 245 provides more direct access to the servers of server systems 210, and while not necessarily providing the full web functionality provided by web server 240, can be used to support a mobile application on one or more of clients 225. As will be appreciated in light of the present disclosure, while such communications paths are depicted in the foregoing manner, such an architecture is merely an example of such communications paths. Any number of alternatives are possible in this regard, and are intended to come within the scope of the present disclosure.

Figure 3:
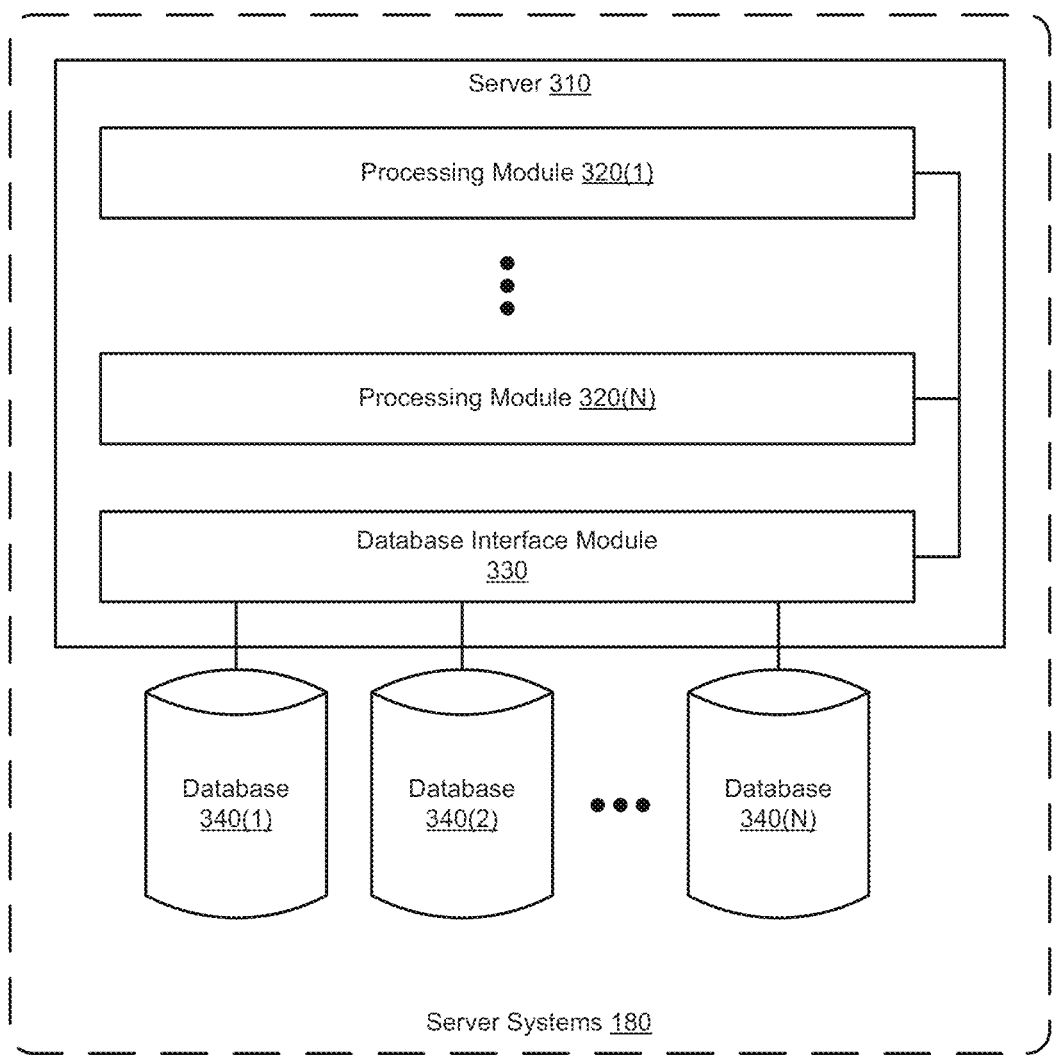
FIG. 3 is a block diagram illustrating an example of a generic server architecture, according to methods and systems such as those disclosed herein.

FIG. 3 is a block diagram illustrating an example of a generic server architecture, according to methods and systems such as those disclosed herein. FIG. 3 thus depicts a generic server architecture 300 that can be used to implement one or more of the server systems of server systems 180. A server of server systems 180 (depicted in FIG. 3 as a server 310) will thus include, typically, a number of components that support the maintenance and retrieval of digital information. For example, such components can include one or more processing modules (depicted in FIG. 3 as processing modules 320(1)-(N), a database interface module (depicted in FIG. 3 as a database interface module 330), and one or more databases (depicted in FIG. 3 as databases 340(1)-(N)). Generally, databases 340(1)-(N) store digital information pertinent to the processing performed by processing modules 320(1)-(N). Database interface module 330 provides one or more of processing modules 320(1)-(N) with access to databases 340(1)-(N). Additionally, database interface module 330 can provide other servers of the given server systems, as well as other components of the distributed manufacturing system, with access to databases 340(1)-(N). As noted, an example of such access is depicted in FIG. 2 by the various communications paths illustrated therein.

Figure 4:
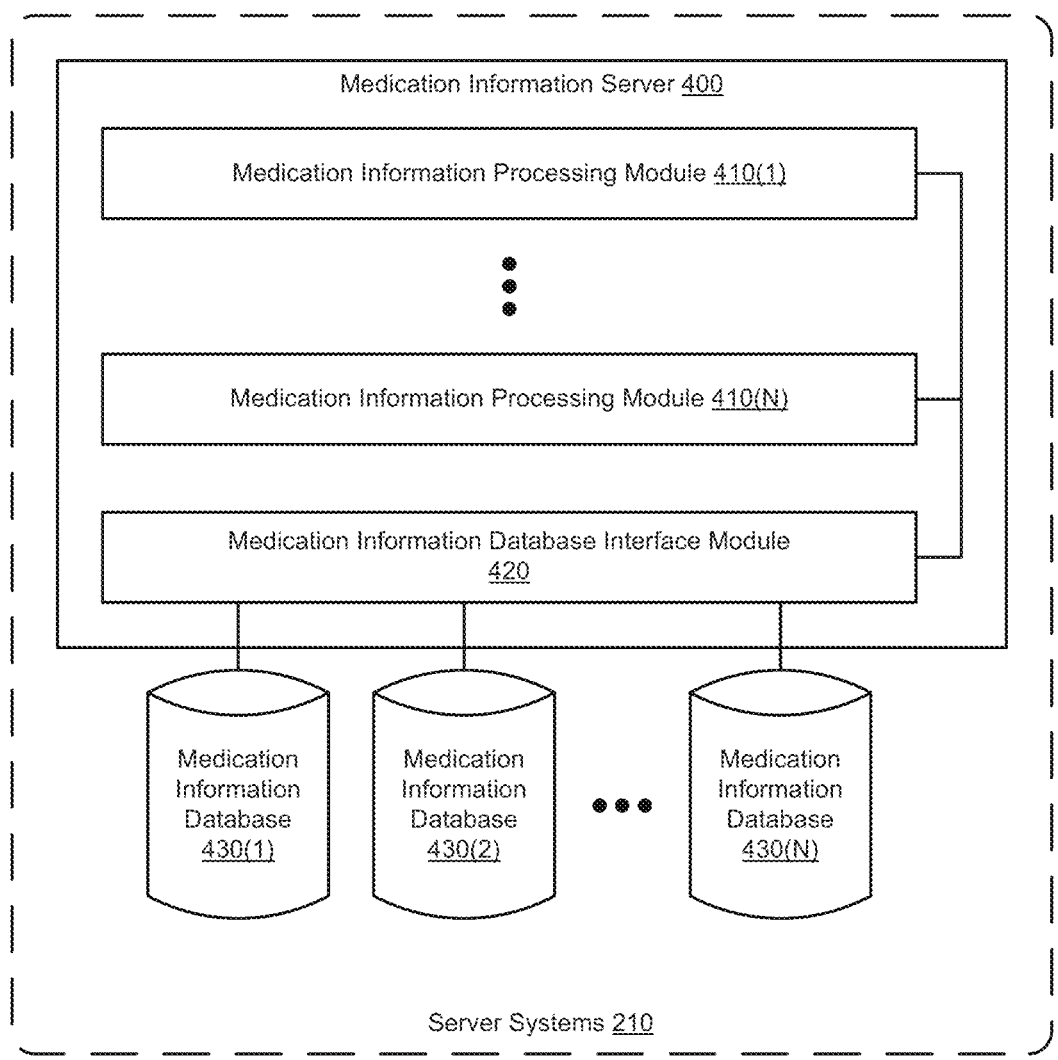
FIG. 4 is a block diagram illustrating an example of a medication information server, according to methods and systems such as those disclosed herein.

FIG. 4 is a block diagram illustrating an example of a medical information server, according to methods and systems such as those disclosed herein. In the manner of generic server architecture 300, a medical information server of server systems 210 is depicted as a medical information server 400. In the manner of generic server architecture 300, then, medical information server 400 includes one or more medical information processing modules (depicted in FIG. 4 as medical information processing modules 410(1)-(N), a number of medical information databases (depicted in FIG. 4 as medical information databases 430(1)-(N)), and interfacing such medical information processing modules and medical information databases, a medical information database interface module (depicted in FIG. 4 as a medical information database interface module 420). To this end, medical information database interface module 420 can provide other servers of server systems 210, as well as other components of the distributed manufacturing system, with access to medical information databases 430. For example, as depicted in FIG. 2, medical information database interface module 420 provides production server 262, customization server 266, and web server 268 with access to medical information databases 430 via one of the two communication paths depicted therein. A specific and more detailed implementation of a medical information server, with regard to the distributed production and shipping/delivery of greeting cards, is provided subsequently.

Figure 5:
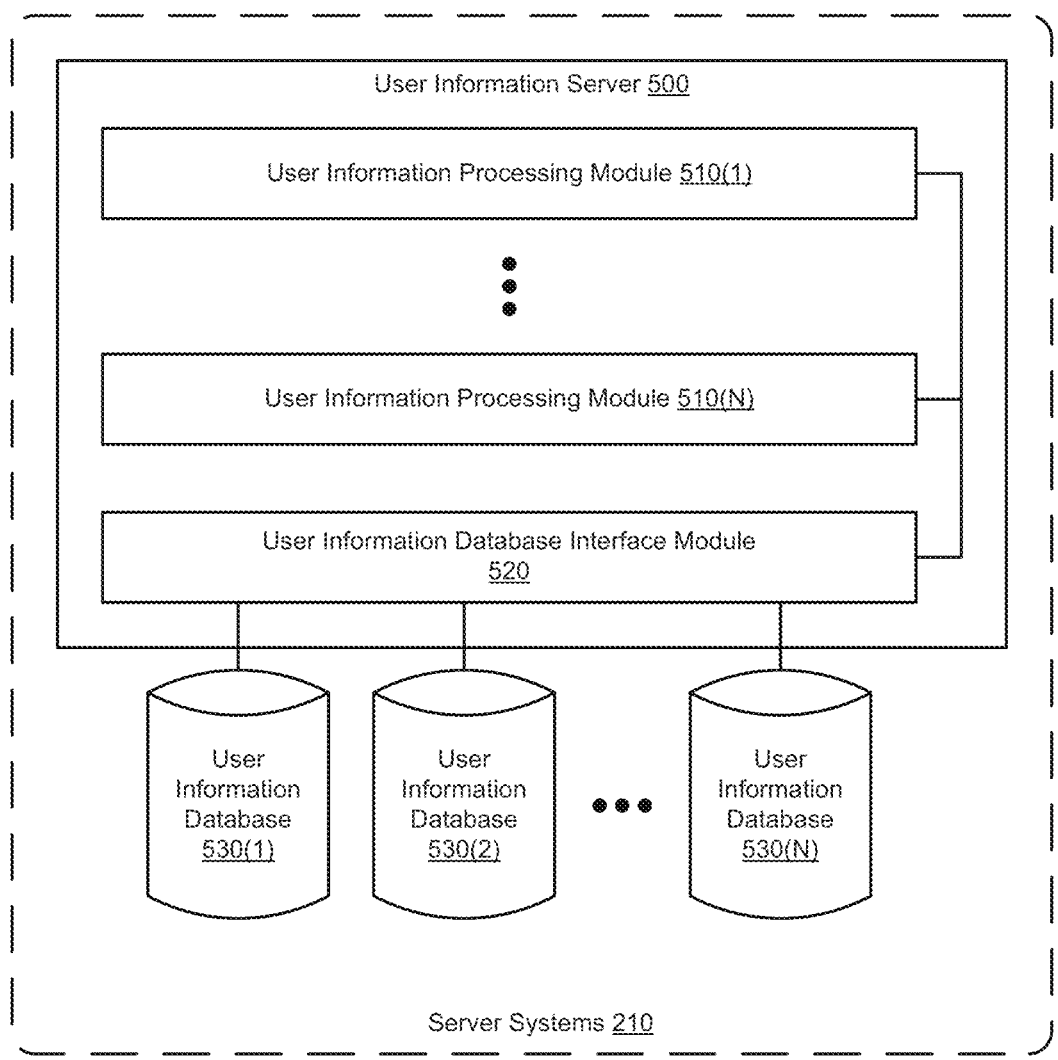
FIG. 5 is a block diagram illustrating an example of a user information server, according to methods and systems such as those disclosed herein.

FIG. 5 is a block diagram illustrating an example of a user information server, according to methods and systems such as those disclosed herein. In the manner noted, server systems 210 can also include one or more user information servers, an example of which is depicted in FIG. 5 as a user information server 500. User information server 500 includes one or more user information processing modules (depicted in FIG. 5 as user information processing modules 510(1)-(N)), which can be accessed by one or more clients such as clients 225 of FIG. 2. User information processing modules 510(1)-(N) can be implemented to support the provision and maintenance of user information (e.g., both for users of the system and patience) in the identification and selection of medications, as well as information related thereto, such as those mentioned earlier, for example.

In turn, user information processing modules 510 interface via a user information database interface module 520, with one or more user information databases (depicted in FIG. 5 as user information databases 530(1)-(N)). User information databases 530 maintain digital information regarding users and patience, as well as medication information for those patients. In addition to user information processing modules 510 being able to communicate with one another, user information processing modules 510 are able to maintain digital information in one or more of user information databases 530 via user information database interface module 520.

Additionally, user information database interface module 520 can provide other servers of server systems 210, as well as other components of such systems, with access to both user information databases and medical information databases (e.g., by way of cross-referencing to such databases). For example, as depicted in FIG. 2, user information database interface module 520 can provide access to user information databases 532 other of the servers of server systems 210 via one of the communication paths depicted therein. A specific and more detailed implementation of a medical information server, with regard to the receipt of patient information and transmission of medication information, is provided subsequently.

Figure 6:
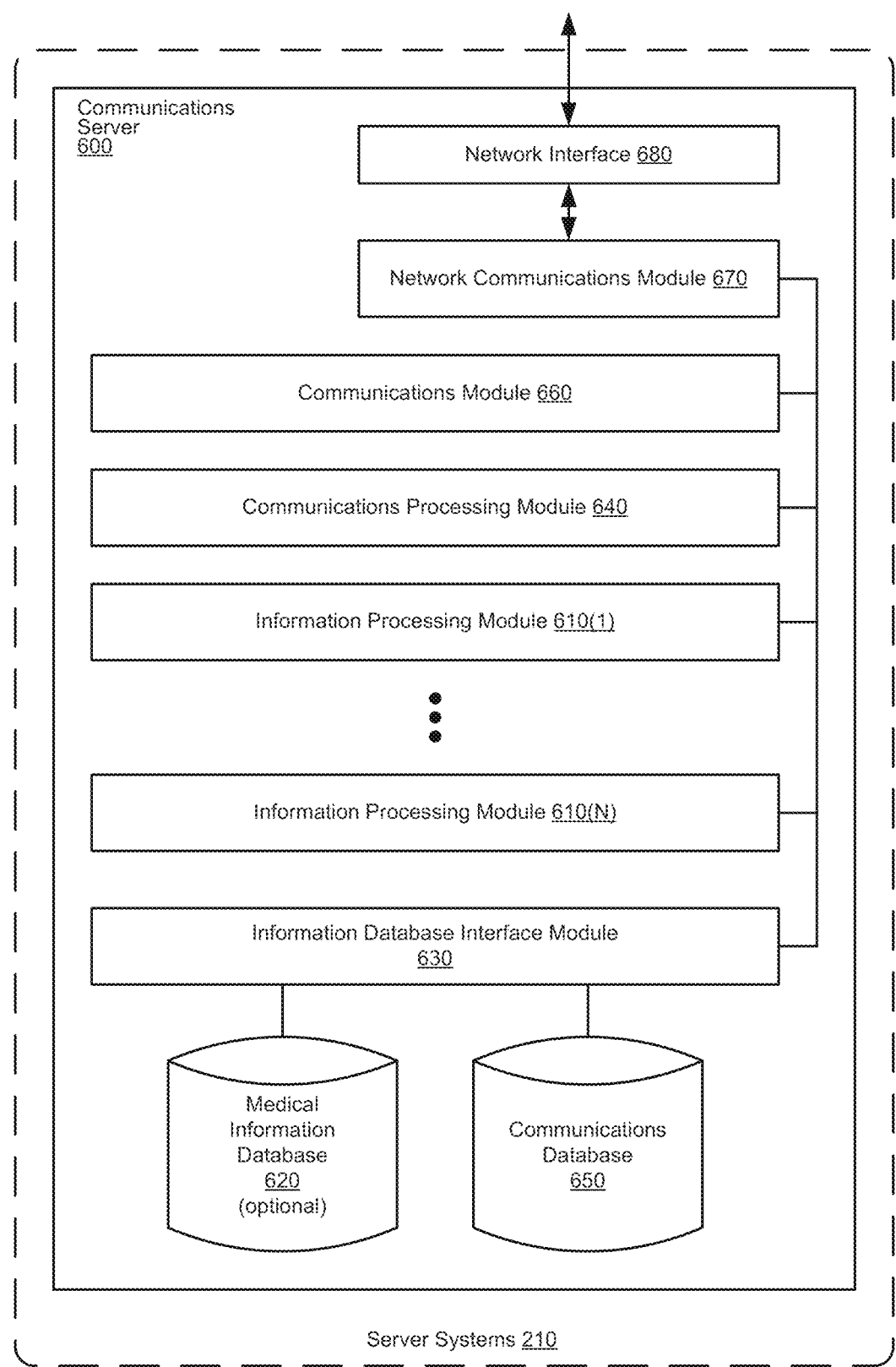
FIG. 6 is a block diagram illustrating an example of a communication server, according to methods and systems such as those disclosed herein.

FIG. 6 is a block diagram illustrating an example of a communication server, according to methods and systems such as those disclosed herein. In certain embodiments, server systems 210 will include for such purposes one or more communications servers, such as a communications server 600. Communications server 600 includes a number of components that support communications with, for example, an application executed by a mobile device (e.g., one or more of clients 125 of FIG. 1 (including one or more of the mobile devices depicted therein) and/or one or more of clients 225 of FIG. 2) and the provision/receipt of the requisite digital information to/from the given mobile device(s), thereby facilitating the gathering of information (e.g., user information, patient information (including physical characteristics), symptom information, current medications, and/or the like) and presentation of information regarding one or more medications identified. An example implementation of processes in this regard is provided subsequently.

In one embodiment, communication server 600 includes one or more information processing modules (depicted in FIG. 6 as information processing modules 610(1)-(N)). Information processing modules 610, in certain embodiments, contain the requisite digital information from one or more servers (e.g., the servers of server systems 210). In those or other embodiments, each of information processing modules 610 can be configured to process digital information representing one or more medications and/or patient/user information. Information processing modules 610 can maintain such digital information in, for example, a database (depicted in FIG. 6 as a medical information database 620) by communicating therewith via a information database interface module 630. In turn (or in parallel), one or more determinations can be made as to the manner in which medication information is to be presented.

In support of such operations, information database interface module 630 can provide other servers of server systems 210, as well as other components of medication information system architecture 200, with access to medical information database 620. For example, as depicted in FIG. 2, information database interface module 630 provides the various servers of server systems 210 with access to medical information database 620 via the communication path depicted therein.

Operations such as those described generally above can be carried out by a communications processing module of communications server 600 (such as is depicted in FIG. 6 as a communications processing module 640). In performing such operations and making such determinations, communications processing module 640 can interface, via information database interface module 630, with a communications database (depicted in FIG. 6 as a communications database 650), and in so doing maintain information regarding the topology of a network (e.g., network 220 of FIG. 2).

Example Processes for Relevance-Based Searches of Medication Information

Figure 7:
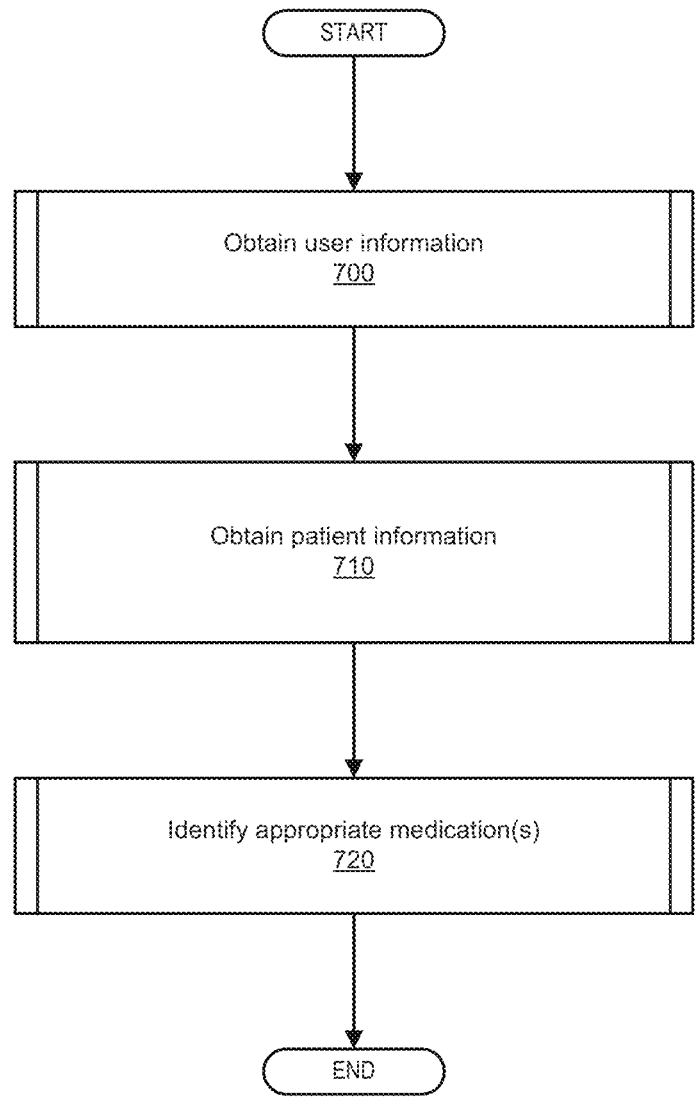
FIG. 7 is a simplified flow diagram illustrating an example of operations performed in identifying one or more medications by way of a medication information system, according to methods and systems such as those disclosed herein.

FIG. 7 is a simplified flow diagram illustrating an example of operations performed in identifying one or more medications by way of a medication information system, according to methods and systems such as those disclosed herein. The process of FIG. 7 begins, in the example illustrated therein, with obtaining user information (700). As noted elsewhere herein, such user information can include login credentials, account information, address information, and other such information. Patient information is then obtained (710). Such patient information can include physical characteristics, one or more symptoms, one or more medications currently being taken, and other such information relevant to identifying one or more medications to be procured (e.g., as by purchase OTC, by prescription, by contacting a physician via telemedicine, or by some other comparable means). Once the relevant patient information is been obtained, one or more appropriate medications can thus be identified. Examples of methods that can be used to perform such identification are described subsequently herein.

Figure 8A:
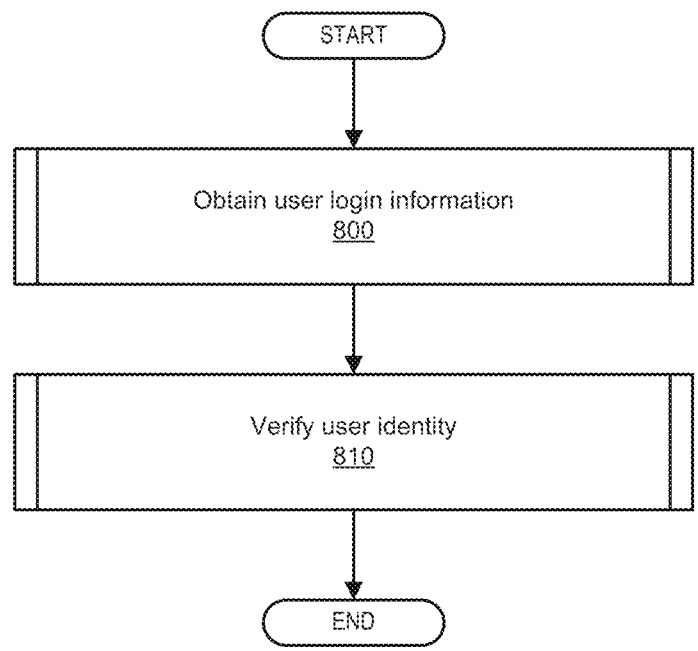
FIG. 8A is a simplified flow diagram illustrating an example of operations performed in obtaining user information, according to methods and systems such as those disclosed herein.

FIG. 8A is a simplified flow diagram illustrating an example of operations performed in obtaining user information, according to methods and systems such as those disclosed herein.

Figure 8B:
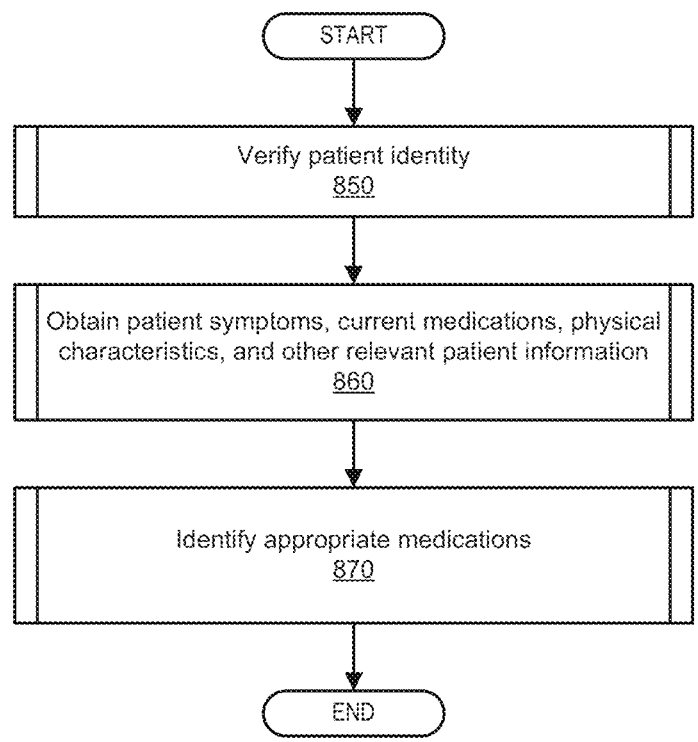
FIG. 8B is a simplified flow diagram illustrating an example of operations performed in obtaining patient information, according to methods and systems such as those disclosed herein.

FIG. 8B is a simplified flow diagram illustrating an example of operations performed in obtaining patient information, according to methods and systems such as those disclosed herein.

Figure 9:
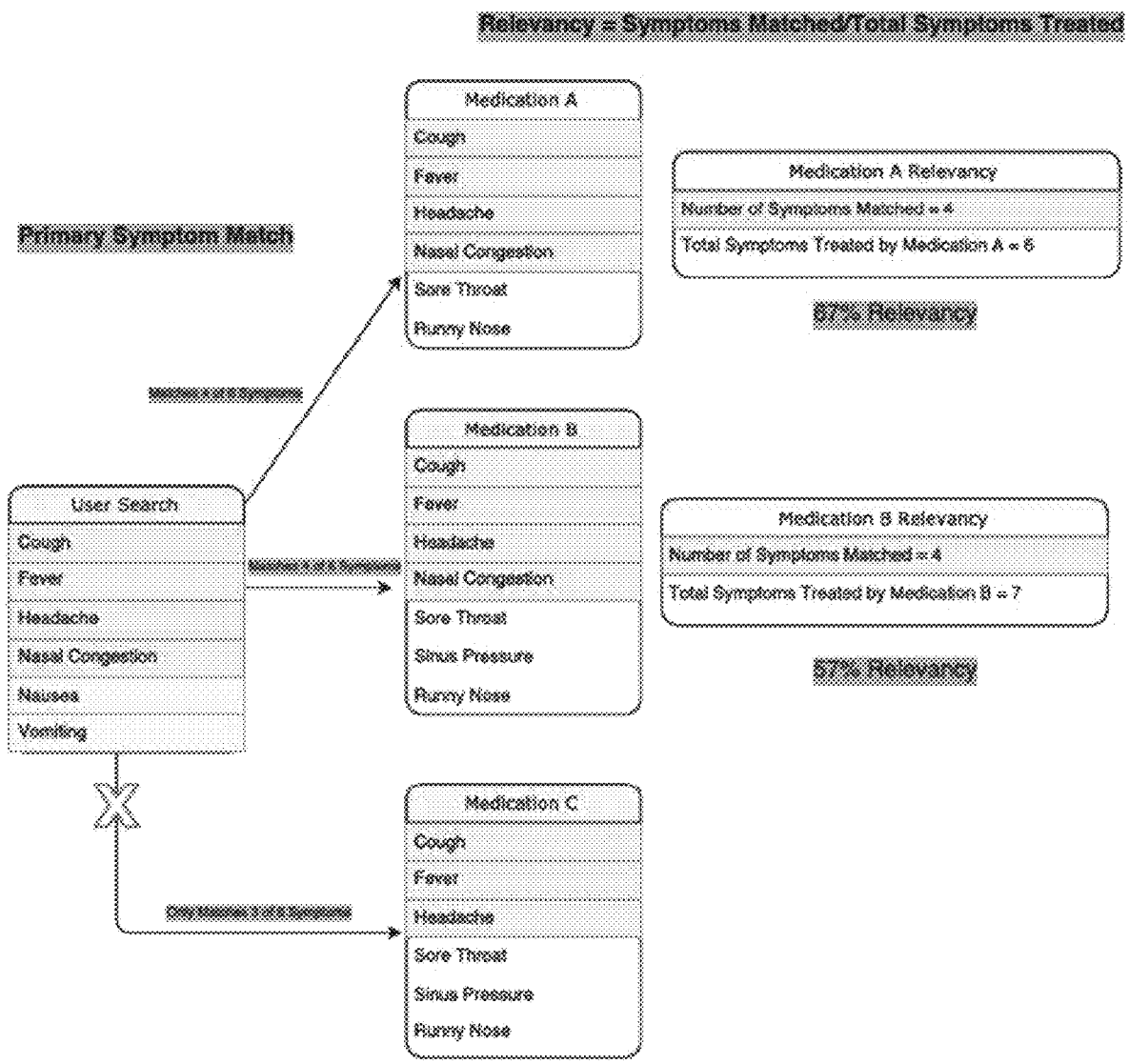
FIG. 9 is a simplified flow diagram illustrating an example of operations performed in searching information, according to methods and systems such as those disclosed herein.

FIG. 9 is a simplified flow diagram illustrating an example of operations performed in searching information, according to methods and systems such as those disclosed herein.

Figure 10:
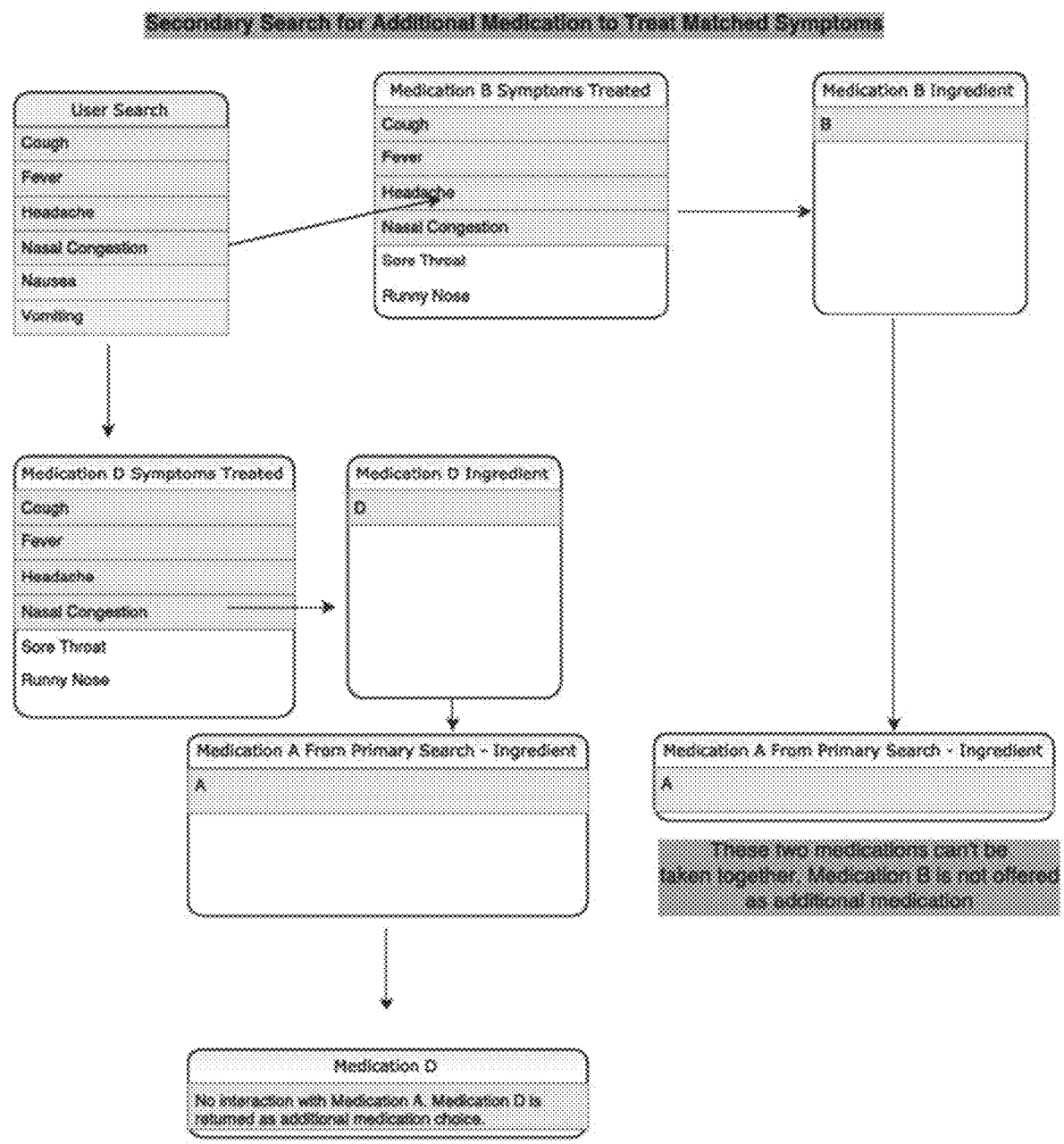
FIG. 10 is a simplified flow diagram illustrating an example of operations performed in searching information, according to methods and systems such as those disclosed herein.

FIG. 10 is a simplified flow diagram illustrating an example of operations performed in searching information, according to methods and systems such as those disclosed herein.

Figure 11:
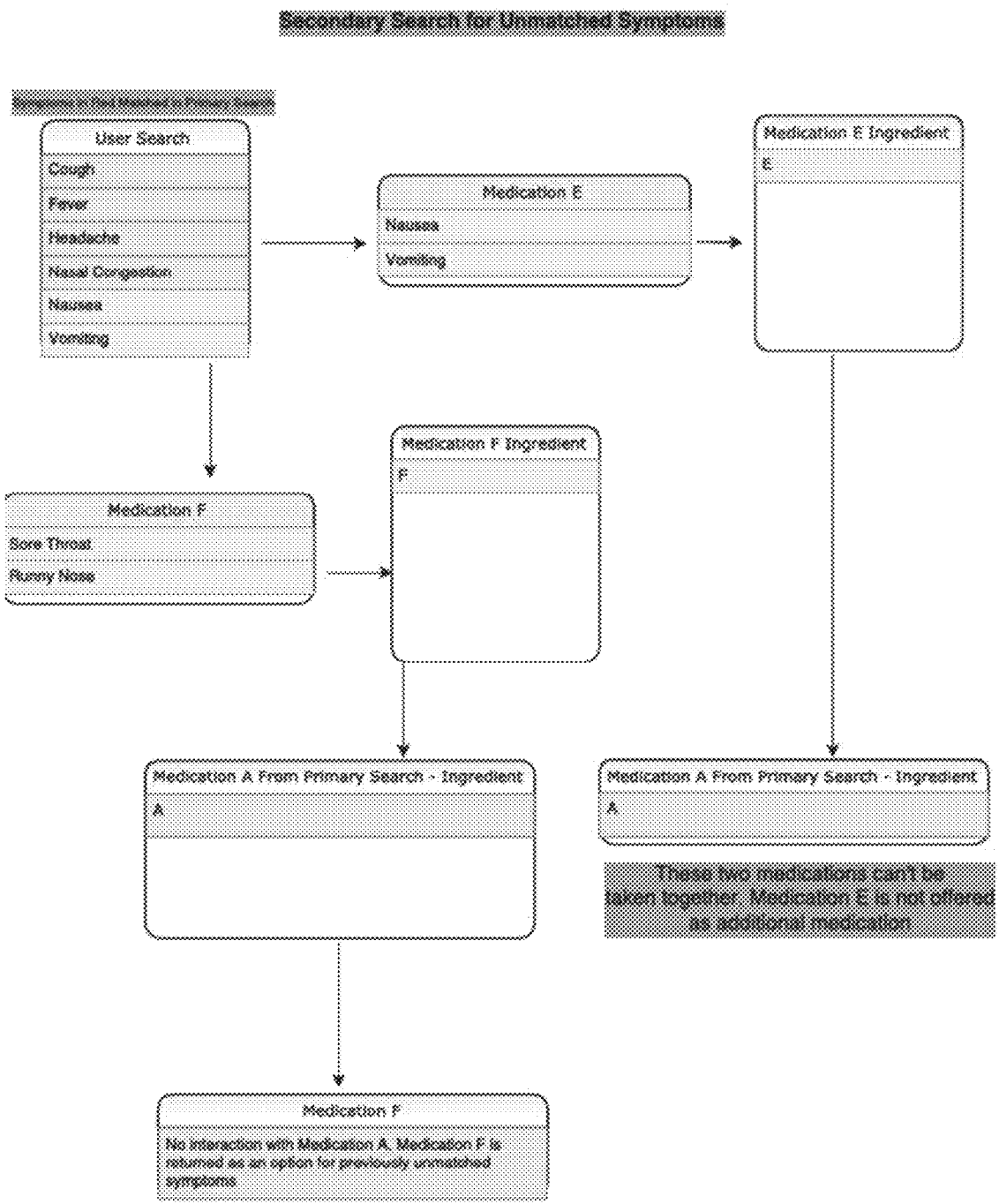
FIG. 11 is a simplified flow diagram illustrating an example of operations performed in searching information, according to methods and systems such as those disclosed herein.

FIG. 11 is a simplified flow diagram illustrating an example of operations performed in searching information, according to methods and systems such as those disclosed herein.

Example User Interface for Relevance-Based Searches of Medication Information

Figure 12:
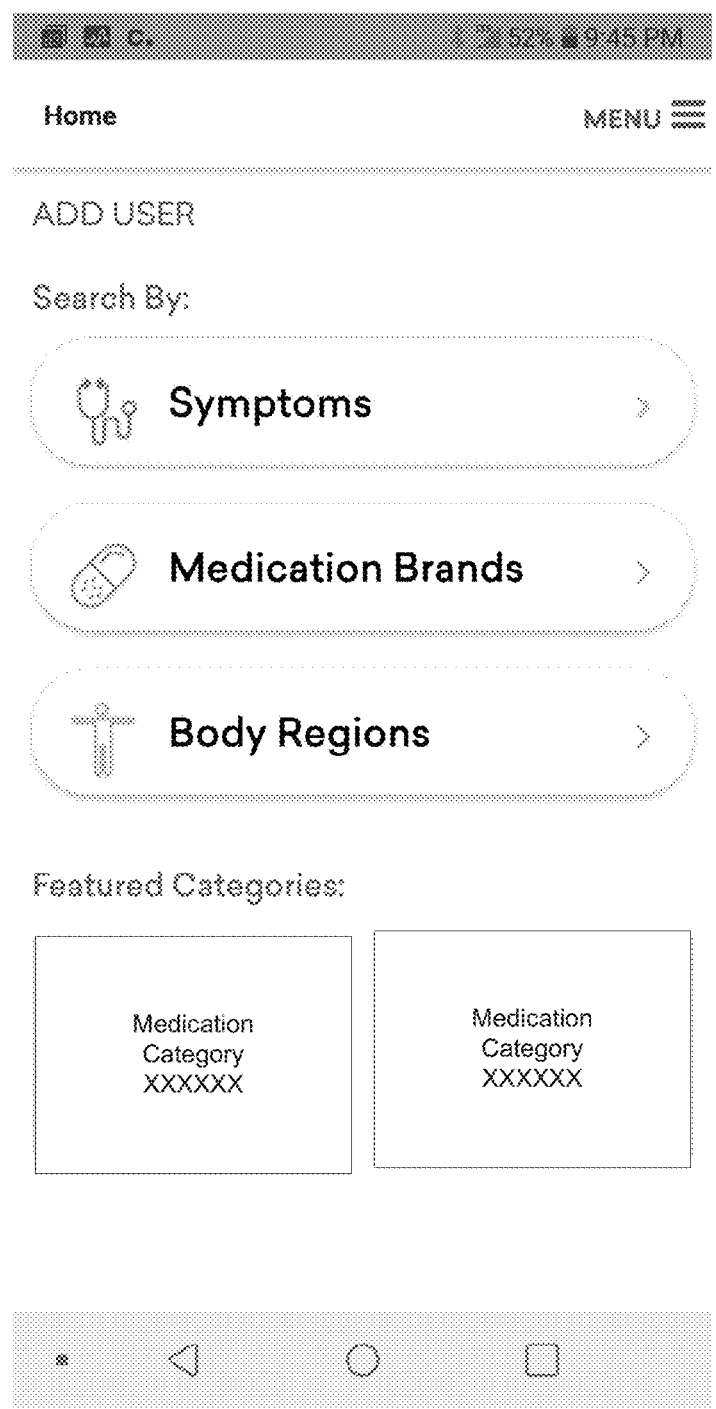
FIG. 12 is a block diagram illustrating an example of a user screen, according to methods and systems such as those disclosed herein.

FIG. 12 is a block diagram illustrating an example of a user screen, according to methods and systems such as those disclosed herein.

Figure 13:
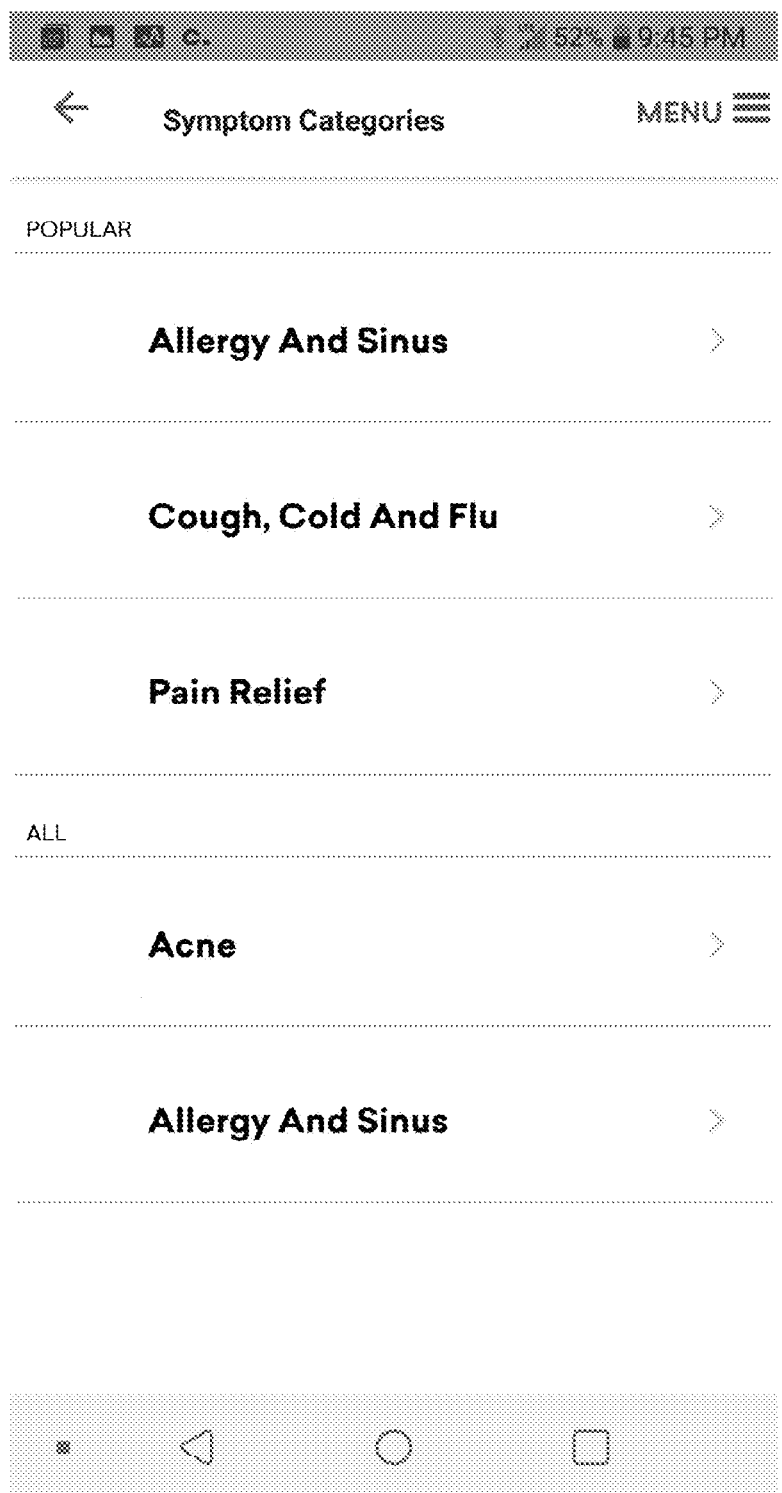
FIG. 13 is a block diagram illustrating an example of a user screen, according to methods and systems such as those disclosed herein.

FIG. 13 is a block diagram illustrating an example of a user screen, according to methods and systems such as those disclosed herein.

Figure 14:
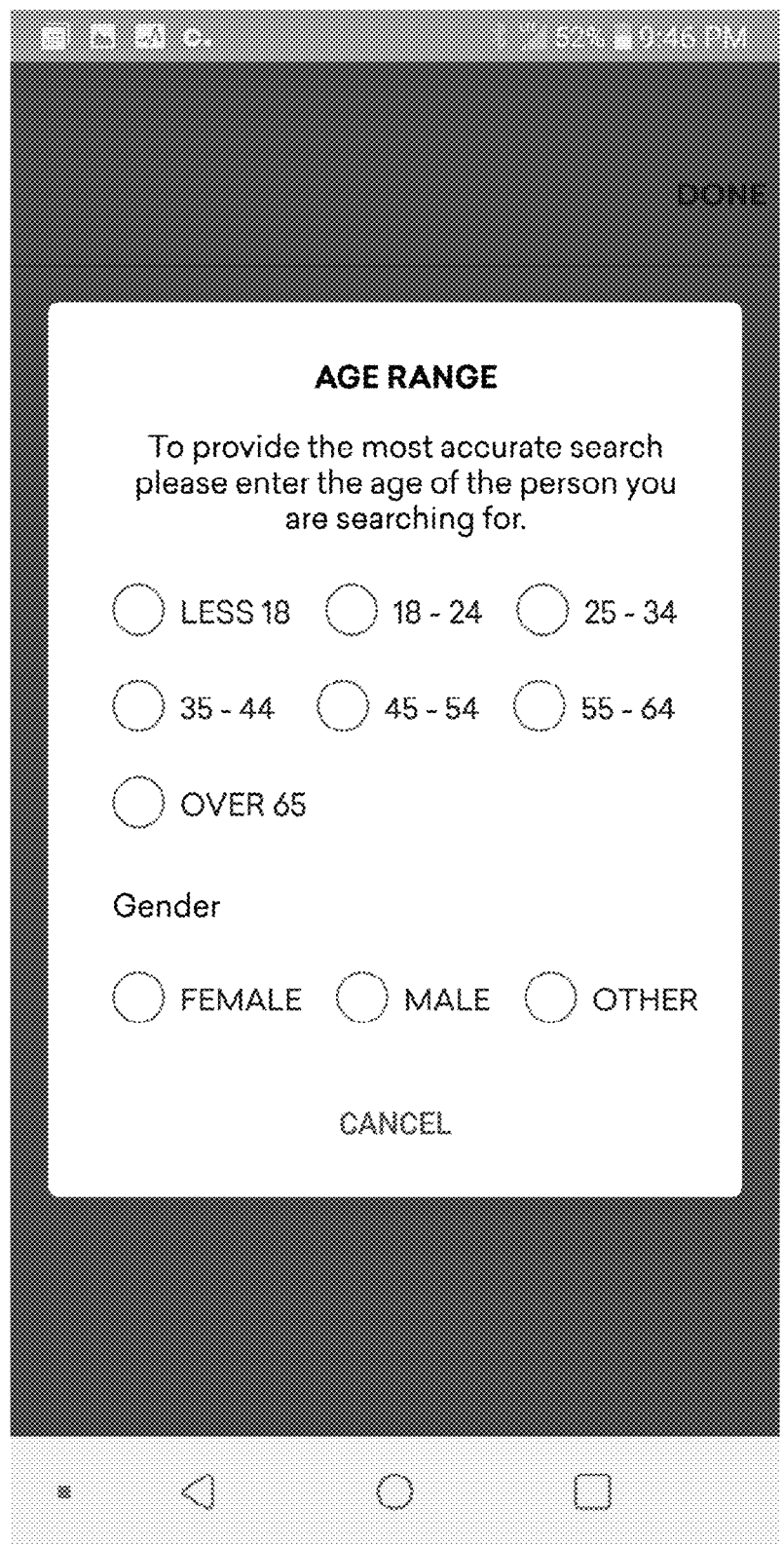
FIG. 14 is a block diagram illustrating an example of a user screen, according to methods and systems such as those disclosed herein.

FIG. 14 is a block diagram illustrating an example of a user screen, according to methods and systems such as those disclosed herein.

Figure 15:
FIG. 15 is a block diagram illustrating an example of a user screen, according to methods and systems such as those disclosed herein.
Figure 15:
Figure 15:
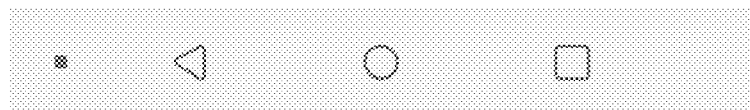

FIG. 15 is a block diagram illustrating an example of a user screen, according to methods and systems such as those disclosed herein.

Figure 16:
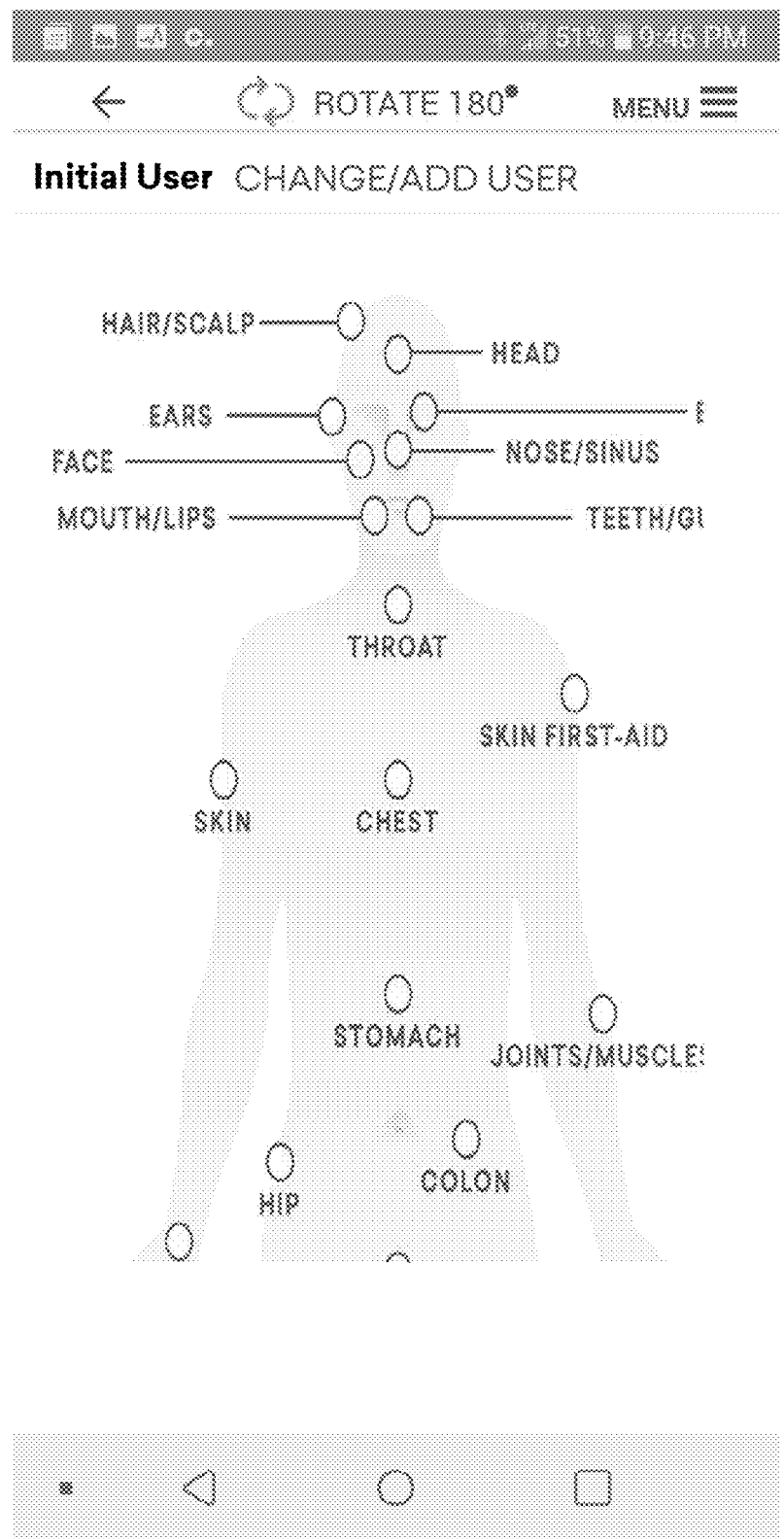
FIG. 16 is a block diagram illustrating an example of a user screen, according to methods and systems such as those disclosed herein.

FIG. 16 is a block diagram illustrating an example of a user screen, according to methods and systems such as those disclosed herein.

Figure 17:
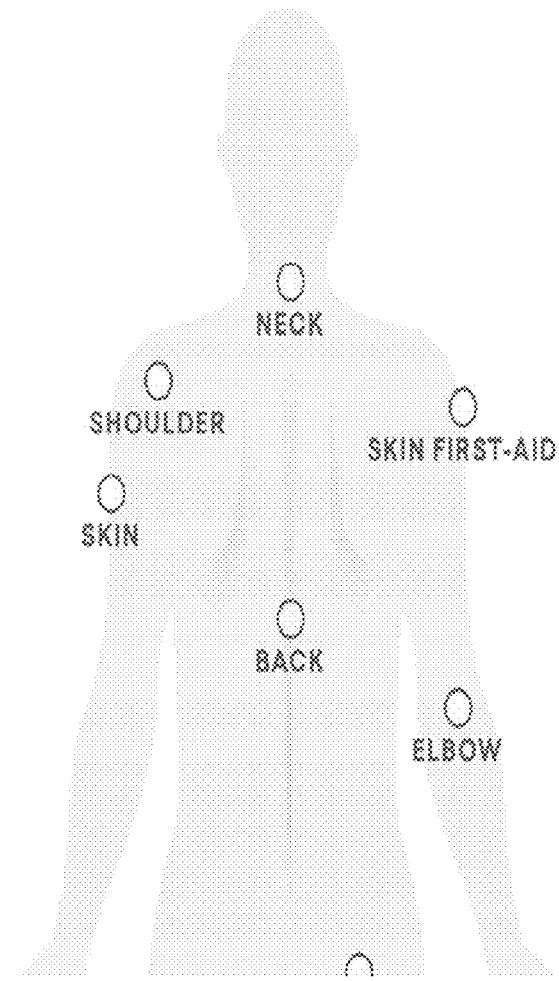
FIG. 17 is a block diagram illustrating an example of a user screen, according to methods and systems such as those disclosed herein.

FIG. 17 is a block diagram illustrating an example of a user screen, according to methods and systems such as those disclosed herein.

An Example of Relevancy-Based Medication Searching

1. Search Relevancy Optimization

If a patient were to complain of a headache and search the term "headache" using an online search engine according to the drug labeling, results might include Tylenol (appropriate) as well as Alka-Seltzer Plus Cold and Flu (and large number of other cold medicines) which also treat headaches and every medicine that contains acetaminophen or ibuprofen or aspirin. Methods and systems such as those disclosed herein provide a system designed to return results that are appropriate to the symptoms being searched, taking into consideration factors such as a patient's physical characteristics, current medications, potential side-effects, patient medication reactions, and other such factors. Using methods and systems such as those described herein, medication identification based on a symptom such as a headache, will identify medications that only treat headaches as being more relevant (and so, rank higher) than those that treat headache plus nasal congestion and cough. In such a case, a user sees plain Tylenol or Motrin before other medications such as Mucinex-DM, Alka-Seltzer Plus Cold and Flu and so forth, are presented. Such methods and systems are also transparent in the presentation of such results, such that the user is able to see at a glance that a medication thus identified is indicated for headaches (pain) or treats headaches and other problems, allowing the user to immediately determine whether a medication might have multiple active ingredients or uses beyond their needs.

2. Vocabulary Reconciliation—Such Functionality can be Accomplished Using a Number of Techniques Similar symptom terms are identified and converted to the same term; example Nasal Congestion was worded in many ways. Such as "treats swelling of the lining of the nose to restore freer breathing" or "for swelling of the passage lining of the nose" etc. We reconciled these terms to create a richer search.

Similarly dosage forms are consolidated and simplified . . . .

Enema was identified as a liquid, we classified as an enema to avoid confusion.

Capsules, LiquiCaps, Liquigels, Coated Capsules were combined to a common format.

Effervescent tablets were reclassified as dissolvable

3. Safety Constraints—for Example, when Searching for Children's Medications, Other Medications) e.g., Such as Medications for Adults) are not Shown.

The advantages of methods and systems such as those disclosed herein are numerous, and include the ability to apply novel search techniques to the identification of one or more appropriate medications, based on patient information including, for example, physical characteristics, symptoms, and the like. Such methods and systems can include a combination of FDA information, Manufacturers claims and open source material. Further, specific medication information formats can be employed to make such searching functionality more efficient. Further still, unique medication codes can be employed to better identify a specific medication (e.g., a branded medication), one or more important active ingredients, and other such considerations.

Search Algorithm—Relevancy of Results Determined by

1. Step1: Medication that matches the highest number of symptoms searched for
   a. If a user uses 5 search terms a medication that treats 4 of them will appear before a medication that matches 3
2. Step 2: A reverse match is performed of the medications that match the most symptoms of Step 1
   a. Explanation: In step 1 assume two medications treat 4 of the 5 symptoms searched for.
   b. Let's call them medication A and medication B
   c. Medication A treats 9 symptoms in total
   d. Medication B treats 6 symptoms in total
   e. 4 is the total number of matches—it becomes the numerator
   f. For medication A 4/9=44% relevancy
   g. For medication B 4/6=67% relevancy
   h. Medication B is returned above medication A Second Medication for Same Symptoms Recommendation 1. All of the active ingredients in our database have a unique number. Sometimes there are additional medications that treat the same 4 symptoms matched by medication B above. These additional medications are offered if they don't duplicate the active ingredients in medication B. (We will call this second medication suggestion Medication C)

Secondary Search for Additional Symptoms

1. For the symptoms that are not covered by Medication B then a secondary search is performed for a medication that treats any of the remaining symptoms. Any medications that treats these remaining symptoms are returned if the active ingredients of the secondary search don't overlap or conflict with the active ingredients in medication B (or C if applicable.)

Functionalities provided by a mobile application according to methods and systems such as those described herein include the following:

Authenticate
Authenticate a device
Authenticate a User
Pricing
Get Price information for a medication
Medications
Get medication brands
Get medication facts sections and disclaimers
Pharmacies
Locate nearest Stores for a medication by latitude and longitude
Reviews
Add a new review
Get top n reviewed symptoms
Get top n reviews
Search
Search medication by set id
Search medications by brand
Search medications by symptoms
Symptoms
Search by anatomical features
Search by Symptoms
Appendices Please refer to Appendices A and B, which appear below and are incorporated herein by reference, in its entirety and for all purposes, and which provides further disclosure of the concepts described herein.

An Example Computing and Network Environment

As shown above, the systems described herein can be implemented using a variety of computer systems and networks. Examples of such computing and network environments are described below with reference to FIGS. 18 and 19.

Figure 18:
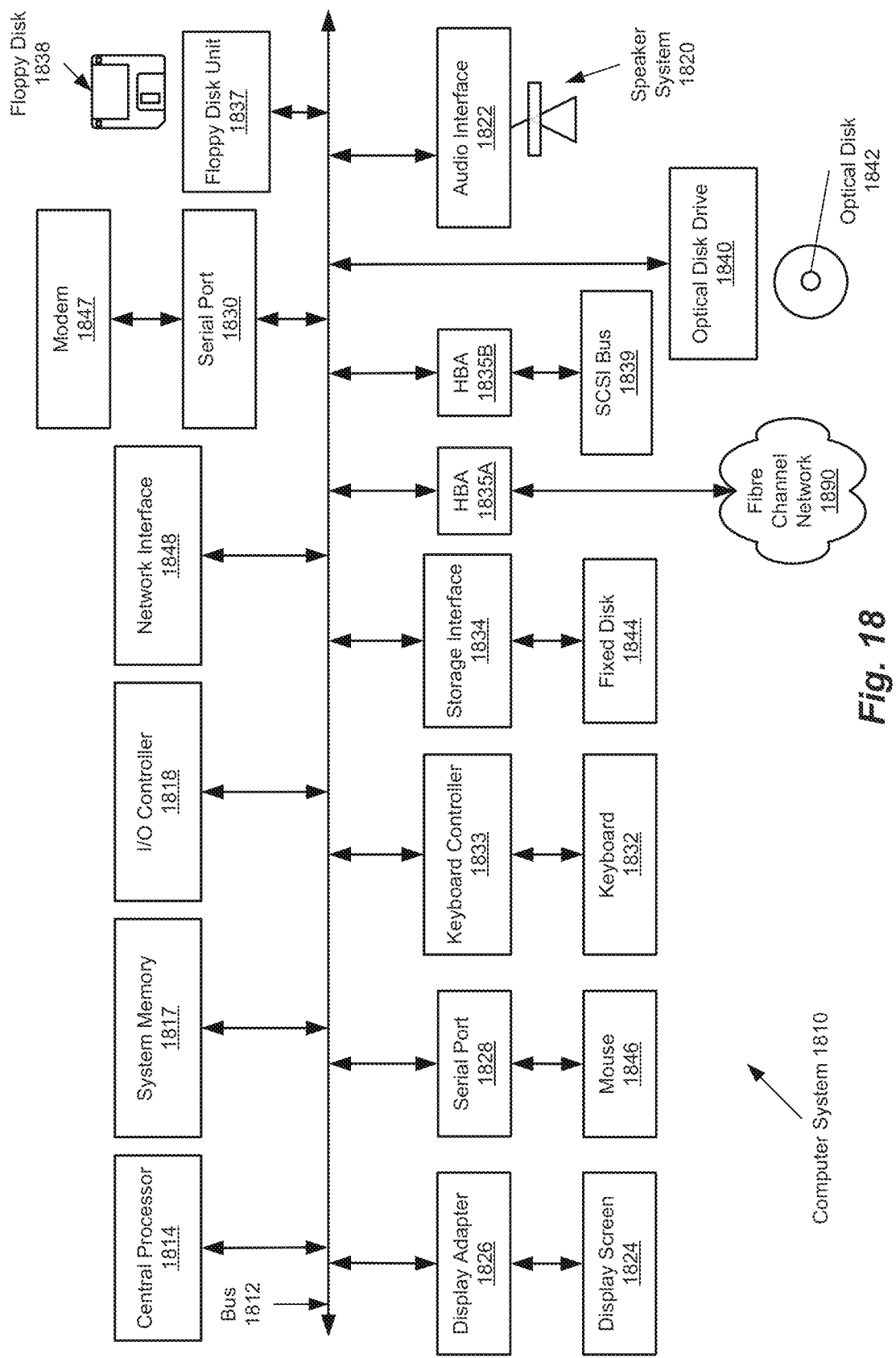
FIG. 18 is a block diagram depicting a computer system suitable for implementing aspects of systems according to embodiments of systems such as those disclosed herein.

FIG. 18 depicts a block diagram of a computer system 1810 suitable for implementing aspects of the systems described herein, and the like. Computer system 1810 includes a bus 1812 which interconnects major subsystems of computer system 1810, such as a central processor 1814, a system memory 1817 (typically RAM, but which may also include ROM, flash RAM, or the like), an input/output controller 1818, an external audio device, such as a speaker system 1820 via an audio output interface 1822, an external device, such as a display screen 1824 via display adapter 1826, serial ports 1828 and 1830, a keyboard 1832 (interfaced with a keyboard controller 1833), a storage interface 1834, a floppy disk drive 1837 operative to receive a floppy disk 1838, a host bus adapter (HBA) interface card 1835A operative to connect with a Fibre Channel network 1890, a host bus adapter (HBA) interface card 1835B operative to connect to a SCSI bus 1839, and an optical disk drive 1840 operative to receive an optical disk 1842. Also included are a mouse 1846 (or other point-and-click device, coupled to bus 1812 via serial port 1828), a modem 1847 (coupled to bus 1812 via serial port 1830), and a network interface 1848 (coupled directly to bus 1812).

Bus 1812 allows data communication between central processor 1814 and system memory 1817, which may include read-only memory (ROM) or flash memory (neither shown), and random access memory (RAM) (not shown), as previously noted. RAM is generally the main memory into which the operating system and application programs are loaded. The ROM or flash memory can contain, among other code, the Basic Input-Output System (BIOS) which controls basic hardware operation such as the interaction with peripheral components. Applications resident with computer system 1810 are generally stored on and accessed from a computer-readable storage medium, such as a hard disk drive (e.g., fixed disk 1844), an optical drive (e.g., optical drive 1840), a floppy disk unit 1837, or other computer-readable storage medium.

Storage interface 1834, as with the other storage interfaces of computer system 1810, can connect to a standard computer-readable medium for storage and/or retrieval of information, such as a fixed disk drive 1844. Fixed disk drive 1844 may be a part of computer system 1810 or may be separate and accessed through other interface systems. Modem 1847 may provide a direct connection to a remote server via a telephone link or to the Internet via an internet service provider (ISP). Network interface 1848 may provide a direct connection to a remote server via a direct network link to the Internet via a point of presence. Network interface 1848 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 18 need not be present to practice the systems described herein. The devices and subsystems can be interconnected in different ways from that shown in FIG. 18. The operation of a computer system such as that shown in FIG. 18 is readily known in the art and is not discussed in detail in this application. Code to implement the modules of the systems described herein can be stored in computer-readable storage media such as one or more of system memory 1817, fixed disk 1844, optical disk 1842, or floppy disk 1838. The operating system provided on computer system 1810 may be MS-WINDOWS®, UNIX®, Linux®, or other operating system.

Further, and as will be appreciated in light of the present disclosure, each of the operations described herein may be executed by a module (e.g., a software module) or a portion of a module, or a computer system user. Thus, the above-described method, the operations thereof and modules therefor may be executed on a computer system configured to execute the operations of the method and/or may be executed from computer-readable storage media. The method may be embodied in a machine-readable and/or computer-readable storage medium for configuring a computer system to execute the method. Thus, the software modules may be stored within and/or transmitted to a computer system memory to configure the computer system to perform the functions of the module.

The software modules described herein may be received by a computer system, for example, from computer-readable storage media. Such computer readable storage media may be permanently, removably or remotely coupled to the computer system. Computer-readable storage media may non-exclusively include, for example, any number of the following: magnetic storage media (including disk and tape storage media); optical storage media such as compact disk media (e.g., CD ROM, CD R, etc.) and digital video disk storage media; nonvolatile memory storage memory including semiconductor-based memory units such as FLASH memory, EEPROM, EPROM, ROM or application specific integrated circuits; and volatile storage media (including registers, buffers or caches, main memory, RAM, etc.). In a UNIX-based embodiment, the software modules may be embodied in a file, which may be a device, a terminal, a local or remote file, a socket, or other such element. Other new and various types of computer-readable storage media may also be used to store the software modules discussed herein.

Many other devices or subsystems (not shown) may be connected in a similar manner (e.g., bar code readers, document scanners, digital cameras and so on). Conversely, it is not necessary for all of the devices shown in FIG. 18 to be present to practice the present invention. The devices and subsystems may be interconnected in different ways from that shown in FIG. 18. The operation of a computer system such as that shown in FIG. 18 is readily known in the art and is not discussed in detail in this application. Code to implement the present invention may be stored in computer-readable storage media such as one or more of system memory 1816, fixed disk 1844, CD-ROM 1842, or floppy disk 1838. Additionally, computer system 1810 may be any kind of computing device, and so includes personal data assistants (PDAs), network appliance, X-window terminal or other such computing device. Computer system 1810 also supports a number of Internet access tools, including, for example, an HTTP-compliant web browser having a JavaScript interpreter, such as FIREFOX, INTERNET EXPLORER, and the like.

Moreover, regarding the signals described herein, those skilled in the art will recognize that a signal may be directly transmitted from a first block to a second block, or a signal may be modified (e.g., amplified, attenuated, delayed, latched, buffered, inverted, filtered or otherwise modified) between the blocks. Although the signals of the above described embodiment are characterized as transmitted from one block to the next, other embodiments of the present invention may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Figure 19:
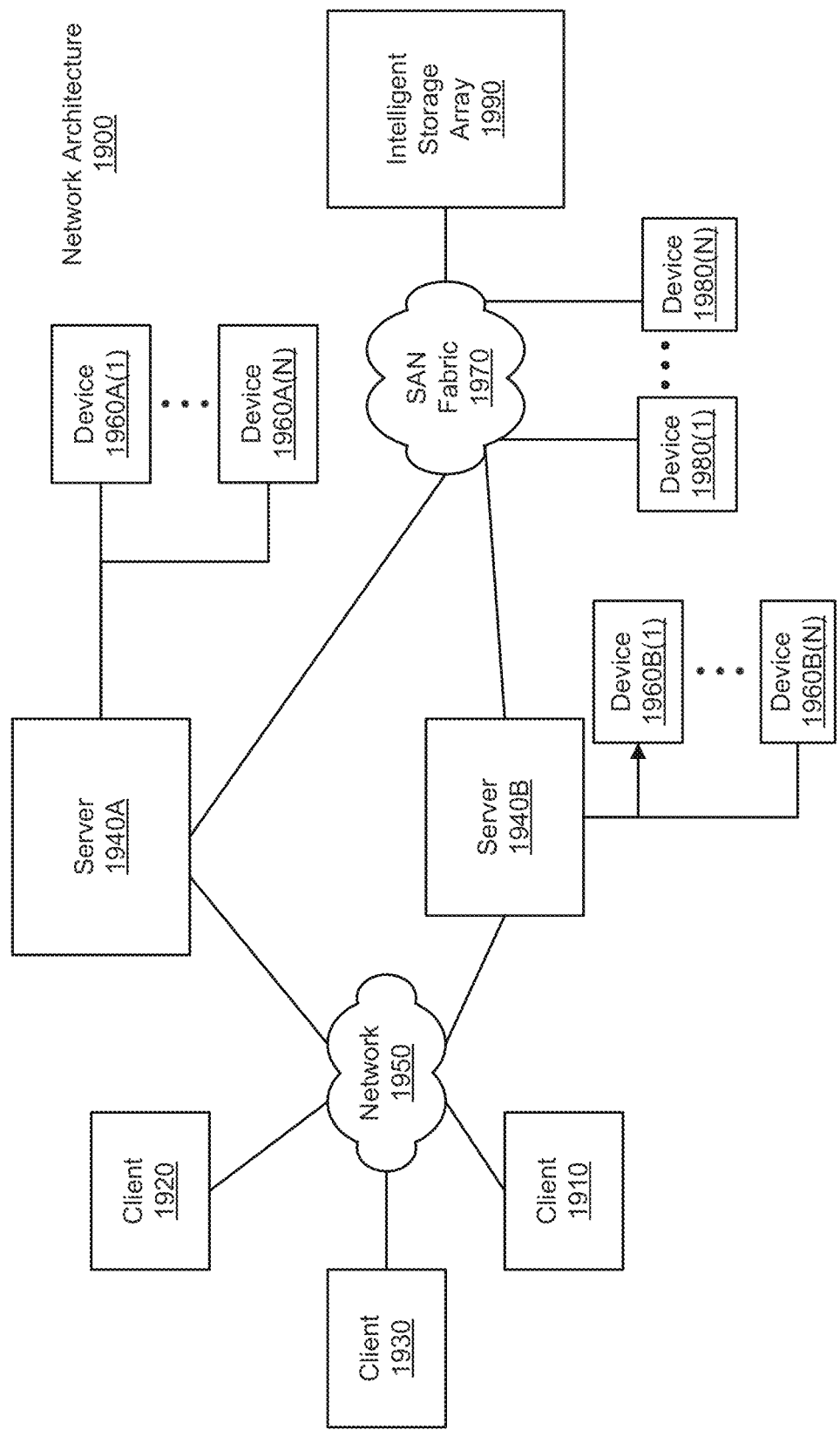
FIG. 19 is a block diagram depicting a network architecture suitable for implementing aspects of systems according to embodiments of systems such as those disclosed herein.

FIG. 19 is a block diagram depicting a network architecture 1900 in which client systems 1910, 1920 and 1930, as well as storage servers 1940A and 1940B (any of which can be implemented using computer system 1910), are coupled to a network 1950. Storage server 1940A is further depicted as having storage devices 1960A(1)-(N) directly attached, and storage server 1940B is depicted with storage devices 1960B(1)-(N) directly attached. Storage servers 1940A and 1940B are also connected to a SAN fabric 1970, although connection to a storage area network is not required for operation. SAN fabric 1970 supports access to storage devices 1980(1)-(N) by storage servers 1940A and 1940B, and so by client systems 1910, 1920 and 1930 via network 1950. Intelligent storage array 1990 is also shown as an example of a specific storage device accessible via SAN fabric 1970.

With reference to computer system 1810, modem 1847, network interface 1848 or some other method can be used to provide connectivity from each of client computer systems 1910, 1920 and 1930 to network 1950. Client systems 1910, 1920 and 1930 are able to access information on storage server 1940A or 1940B using, for example, a web browser or other client software (not shown). Such a client allows client systems 1910, 1920 and 1930 to access data hosted by storage server 1940A or 1940B or one of storage devices 1960A(1)-(N), 1960B(1)-(N), 1980(1)-(N) or intelligent storage array 1990. FIG. 18 depicts the use of a network such as the Internet for exchanging data, but the systems described herein are not limited to the Internet or any particular network-based environment.

The foregoing described embodiments wherein the different components are contained within different other components (e.g., the various elements shown as components of computer system 1810) are merely intended to serve as examples. It is to be understood that such depicted architectures are such, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality.

Other Embodiments

The systems described herein are well adapted to attain the advantages mentioned as well as others inherent therein. While such systems have been depicted, described, and are defined by reference to particular descriptions, such references do not imply a limitation on the claims, and no such limitation is to be inferred. The systems described herein are capable of considerable modification, alteration, and equivalents in form and function, as will occur to those ordinarily skilled in the pertinent arts in considering the present disclosure. The depicted and described embodiments are examples only, and are in no way exhaustive of the scope of the claims.

The foregoing detailed description has set forth various embodiments of the systems described herein via the use of block diagrams, flowcharts, and examples. It will be understood by those within the art that each block diagram component, flowchart step, operation and/or component illustrated by the use of examples can be implemented (individually and/or collectively) by a wide range of hardware, software, firmware, or any combination thereof.

The systems described herein have been described in the context of fully functional computer systems; however, those skilled in the art will appreciate that the systems described herein are capable of being distributed as a program product in a variety of forms, and that the systems described herein apply equally regardless of the particular type of computer-readable media used to actually carry out the distribution. Examples of computer-readable media include computer-readable storage media, as well as media storage and distribution systems developed in the future.

The above-discussed embodiments can be implemented by software modules that perform one or more tasks associated with the embodiments. The software modules discussed herein may include script, batch, or other executable files. The software modules may be stored on a machine-readable or computer-readable storage media such as magnetic floppy disks, hard disks, semiconductor memory (e.g., RAM, ROM, and flash-type media), optical discs (e.g., CD-ROMs, CD-Rs, and DVDs), or other types of memory modules. A storage device used for storing firmware or hardware modules in accordance with an embodiment can also include a semiconductor-based memory, which may be permanently, removably or remotely coupled to a microprocessor/memory system. Thus, the modules can be stored within a computer system memory to configure the computer system to perform the functions of the module. Other new and various types of computer-readable storage media may be used to store the modules discussed herein.

The above description is intended to be illustrative and should not be taken to be limiting. As will be appreciated in light of the present disclosure, other embodiments are possible. Those skilled in the art will readily implement the steps necessary to provide the structures and the methods disclosed herein, and will understand that the process parameters and sequence of steps are given by way of example only and can be varied to achieve the desired structure as well as modifications that are within the scope of the claims. Variations and modifications of the embodiments disclosed herein can be made based on the description set forth herein, without departing from the scope of the claims, giving full cognizance to equivalents thereto in all respects.

Although the systems described herein have been described in connection with several embodiments, these embodiments and their descriptions are not intended to be limited to the specific forms set forth herein. On the contrary, it is intended that such embodiments address such alternatives, modifications, and equivalents as can be reasonably included within the scope of the appended claims.

What is claimed is:

1. A method, implemented in a computer system, comprising:
for each medication of a plurality of medications, for which medication information is stored in a medication information database, causing the computer system to periodically check an external website to determine whether a corresponding link of a plurality of links is accessible, wherein
the corresponding link is a link to information on the external website regarding the each medication of the plurality of medications, if the link is accessible, and
the each medication of the plurality of medications is uniquely identified by a medication identifier of a plurality of medication identifiers;
receiving a request at the computer system, wherein
the request is received from a mobile application executed by a mobile computing device,
the request comprises first patient information comprises patient symptom information, and
the patient symptom information identifies one or more symptoms experienced by a patient;
obtaining second patient information, wherein
the second patient information is information regarding the patient;
identifying one or more medications of the plurality of medications, wherein
the medication information database comprises
a parameter table comprising
a plurality of parameter records, each of which comprises
a symptom data structure of a plurality of symptom data structures,
medication information regarding a corresponding one of the plurality of medications, and the medication identifier of the corresponding one of the plurality of medications, and the identifying the one or more medications comprises
searching the medication information database, wherein the searching comprises
building a medication information database query using the patient symptom information, and
querying the medication information database using the medication information database query, wherein the querying accesses the plurality of symptom data structures of the parameter table, and
returning a returned medication identifier for each of one or more medications returned by the searching, wherein the returned medication identifier is the medication identifier for the each of the one or more medications returned by the searching; and for the each of the one or more medications,
in response to the corresponding link for the each of the one or more medications being active, providing access to the medication information of the each of the one or more medications by sending the returned medication identifier for the each of the one or more medications to the mobile application.

2. The method of claim 1, wherein
the querying further comprises
identifying at least one medication of the one or more medications by comparing the patient symptom information and symptom information stored in the symptom data structure of the plurality of symptom data structures.

3. The method of claim 2, wherein
the parameter table further comprises
body part information,
the medication information database further comprises a medication category table,
the parameter table is associated with the medication category table in the medication information database,
the medication category table comprises
medication category information, and
the at least one medication is further identified using at least one of
the body part information, or
the medication category information.

4. The method of claim 2, wherein
the medication information database further comprises a medication information table,
the parameter table is associated with the medication information table in the medication information database,
the medication information table comprises
sequence information,
the sequence information is configured to be used to sequence the plurality of medications, and
the identifying the at least one medication further comprises
sequencing the plurality of medications using the sequence information.

5. The method of claim 1, wherein the obtaining the second patient information comprises at least one of:
receiving at least a portion of the second patient information from the mobile application executed by the mobile computing device; or
retrieving the at least a portion of the second patient information from the medical information database.

6. The method of claim 1, wherein
the one or more patient characteristic identifiers comprise one or more of
physical characteristics information regarding one or more physical characteristics of the patient,
physical condition information regarding one or more known physical conditions of the patient,
allergic reaction information regarding one or more medications to which the patient has exhibited an allergic reaction, or
medication information regarding one or more medications taken by the patient.

7. The method of claim 6, wherein
each of the plurality of medications is
an over-the-counter medication, or
a prescription medication.

8. The method of claim 1, wherein the identifying further comprises:
filtering the one or more medications returned by the searching, wherein
the one or more medications returned by the searching comprise one or more identified medications, and
the filtering is performed using one or more factors.

9. The method of claim 8, wherein
the one or more factors comprise at least one of
one or more appropriate applications of the one or more identified medications,
one or more contraindications to the one or more identified medications,
symptomologic information for the one or more identified medications, or
dosing of the one or more identified medications.

10. The method of claim 9, wherein
the second patient information further comprises
medication information regarding one or more medications taken by the patient, and
the one or more factors further comprise
medication interaction information regarding medication interaction between the one or more identified medications and the one or more medications taken by the patient.

11. A non-transitory computer-readable storage medium, comprising program instructions, which, when executed by one or more processors of a computing system, perform a method comprising:
for each medication of a plurality of medications, for which medication information is stored in a medication information database, causing the computer system to periodically check an external website to determine whether a corresponding link of a plurality of links is accessible, wherein
the corresponding link is a link to information on the external website regarding the each medication of the plurality of medications, if the link is accessible, and
the each medication of the plurality of medications is uniquely identified by a medication identifier of a plurality of medication identifiers;
receiving a request at the computer system, wherein
the request is received from a mobile application executed by a mobile computing device,
the request comprises first patient information comprises patient symptom information, and
the patient symptom information identifies one or more symptoms experienced by a patient;

obtaining second patient information, wherein
the second patient information is information regarding the patient;
identifying one or more medications of the plurality of medications, wherein
the medication information database comprises
a parameter table comprising
a plurality of parameter records, each of which comprises
a symptom data structure of a plurality of symptom data structures,
medication information regarding a corresponding one of the plurality of medications, and
the medication identifier of the corresponding one of the plurality of medications, and
the identifying the one or more medications comprises
searching the medication information database, wherein the searching comprises
building a medication information database query using the patient symptom information, and
querying the medication information database using the medication information database query, wherein the querying accesses the plurality of symptom data structures of the parameter table, and
returning a returned medication identifier for each of one or more medications returned by the searching, wherein the returned medication identifier is the medication identifier for the each of the one or more medications returned by the searching; and
for the each of the one or more medications,
in response to the corresponding link for the each of the one or more medications being active, providing access to the medication information of the each of the one or more medications by sending the returned medication identifier for the each of the one or more medications to the mobile application.

12. The non-transitory computer-readable storage medium of claim 11, wherein
the querying further comprises
identifying at least one medication of the one or more medications by comparing the patient symptom information and symptom information stored in the symptom data structure of the plurality of symptom data structures.

13. The non-transitory computer-readable storage medium of claim 12, wherein
the parameter table further comprises
body part information,
the medication information database further comprises a medication category table,
the parameter table is associated with the medication category table in the medication information database,
the medication category table comprises
medication category information, and
the at least one medication is further identified using at least one of
the body part information, or
the medication category information.

14. The non-transitory computer-readable storage medium of claim 12, wherein
the medication information database further comprises a medication information table,
the parameter table is associated with the medication information table in the medication information database,
the medication information table comprises sequence information,
the sequence information is configured to be used to sequence the one or more medications, and
the identifying the at least one medication further comprises sequencing the one or more medications using the sequence information.

15. The non-transitory computer-readable storage medium of claim 11, wherein the obtaining the second patient information comprises at least one of:
receiving at least a portion of the second patient information from the mobile application executed by the mobile computing device; or
retrieving the at least a portion of the second patient information from the medical information database.

16. The non-transitory computer-readable storage medium of claim 11, wherein
the one or more patient characteristic identifiers comprise one or more of
physical characteristics information regarding one or more physical characteristics of the patient,
physical condition information regarding one or more known physical conditions of the patient,
allergic reaction information regarding one or more medications to which the patient has exhibited an allergic reaction, or
medication information regarding one or more medications taken by the patient, and
each of the plurality of medications is
an over-the-counter medication, or
a prescription medication.

17. The non-transitory computer-readable storage medium of claim 11, wherein
the identifying further comprises
filtering the one or more medications returned by the searching, wherein
the one or more medications returned by the searching comprise one or more identified medications,
the filtering is performed using one or more factors, and
the one or more factors comprise at least one of
one or more appropriate applications of the one or more identified medications,
one or more contraindications to the one or more identified medications,
symptomologic information for the one or more identified medications, or
dosing of the one or more identified medications.

18. The non-transitory computer-readable storage medium of claim 17, wherein
the second patient information further comprises
medication information regarding one or more medications taken by the patient, and
the one or more factors further comprise
medication interaction information regarding medication interaction between the one or more identified medications and the one or more medications taken by the patient.

19. A computing system comprising:
one or more processors;
a storage device, wherein
the storage device is coupled to the one or more processors and stores a medication information database; and
a computer-readable storage medium coupled to the one or more processors, comprising program instructions, which, when executed by the one or more processors, perform a method comprising
for each medication of a plurality of medications, for which medication information is stored in the medication information database, causing the computer system to periodically check an external website to determine whether a corresponding link of a plurality of links is accessible, wherein the corresponding link is a link to information on the external website regarding the each medication of the plurality of medications, if the link is accessible, and
the each medication of the plurality of medications is uniquely identified by a medication identifier of a plurality of medication identifiers,
receiving a request at the computer system, wherein
the request is received from a mobile application executed by a mobile computing device,
the request comprises first patient information comprises patient symptom information, and
the patient symptom information identifies one or more symptoms experienced by a patient,
obtaining second patient information, wherein
the second patient information is information regarding the patient,
identifying one or more medications of the plurality of medications, wherein
the medication information database comprises
a parameter table comprising
a plurality of parameter records, each of which comprises
a symptom data structure of a plurality of symptom data structures,
medication information regarding a corresponding one of the plurality of medications, and
the medication identifier of the corresponding one of the plurality of medications, and
the identifying the one or more medications comprises
searching the medication information database, wherein the searching comprises
building a medication information database query using the patient symptom information, and
querying the medication information database using the medication information database query, wherein the querying accesses the plurality of symptom data structures of the parameter table, and
returning a returned medication identifier for each of one or more medications returned by the searching, wherein the returned medication identifier is the medication identifier for the each of the one or more medications returned by the searching, and
for the each of the one or more medications,
in response to the corresponding link for the each of the one or more medications being active, providing access to the medication information of the each of the one or more medications by sending the returned medication identifier for the each of the one or more medications to the mobile application.

20. The computing system of claim 19, wherein the obtaining the second patient information comprises:
receiving a first portion of the patient second information from a mobile application executed by a mobile computing device; and
retrieving a second portion of the second patient information from the medical information database.

* * * * *